United States Patent [19]

Georgi

[11] 4,037,598
[45] July 26, 1977

[54] METHOD AND APPARATUS FOR FLUID FLOW CONTROL

[75] Inventor: Heinz W. Georgi, Del Mar, Calif.

[73] Assignee: Ivac Corporation, San Diego, Calif.

[21] Appl. No.: 496,553

[22] Filed: Aug. 12, 1974

[51] Int. Cl.² .............................................. A61M 5/14
[52] U.S. Cl. ............................ 128/214 E; 128/214 F; 128/DIG. 12; 128/DIG. 13; 222/14; 222/59; 222/63; 222/71
[58] Field of Search ....... 128/214 E, 214 F, DIG. 12, 128/DIG. 13, 14; 222/14, 52, 59, 63, 71, 76; 125/2.06 A, 419 PG

[56] References Cited

U.S. PATENT DOCUMENTS

| | | | |
|---|---|---|---|
| 3,543,752 | 12/1970 | Hosse et al. | 128/214 E |
| 3,554,187 | 1/1971 | Glassner | 128/2.06 A |
| 3,631,860 | 1/1972 | Lopin | 128/419 PG |
| 3,655,095 | 4/1972 | Kienitz | 128/214 E |
| 3,731,679 | 5/1973 | Wilhelmson et al. | 128/214 F |
| 3,736,930 | 6/1973 | Georgi | 128/214 E |
| 3,756,456 | 9/1973 | Georgi | 222/14 |
| 3,790,042 | 2/1974 | McCormick | 128/214 E |

OTHER PUBLICATIONS

Service Manual Pulbication, 500020, IVAC Corporation, 1972.

Primary Examiner—William E. Kamm
Attorney, Agent, or Firm—Fulwider, Patton, Rieber, Lee & Utecht

[57] ABSTRACT

A digital system wherein a wide variety of different electromechanical output control devices, e.g., stepping motor pump or solenoid actuated I.V. tube pincher, is driven by electrical output pulses of varible frequency and pulse width from a digital pulse generation and control system, the frequency and pulse width of the output pulses being selected and controlled by the system to establish drop flow rates with digital precision over an extremely wide dynamic range. Pulse width is determined by the relative states of a pair of digital counters in a digital memory, frequency being determined by a high, preferably non-integral, multiple of the desired drop flow rate. The equivalent of negative pulse width in the digital memory can be effectively utilized to expand the effective dynamic range of the memory for specified types of electromechanical output devices. A start up subsystem temporarily presets the initial pulse rate and speeds up early regulation. Duty cycle limitation and visual output pulse width monitoring is also provided. Appropriate alarms also respond to a variety of out-of-limit conditions.

102 Claims, 31 Drawing Figures

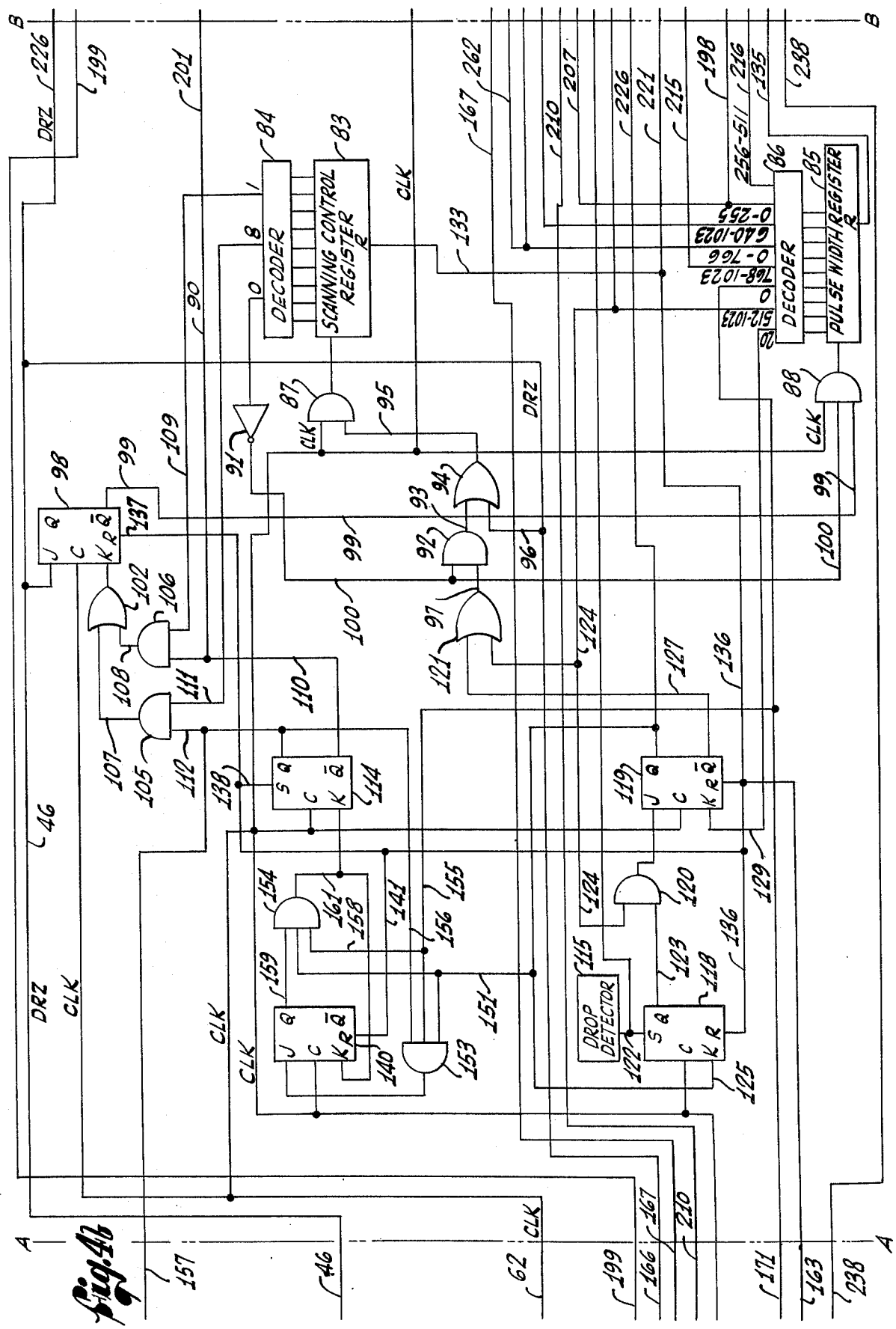

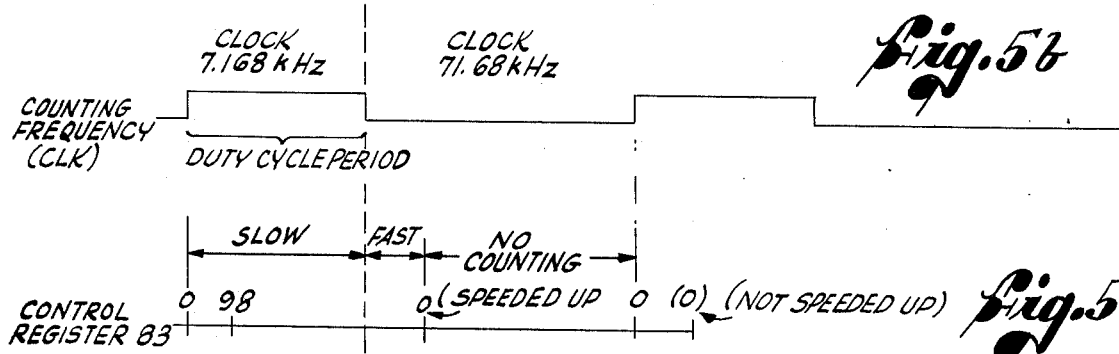
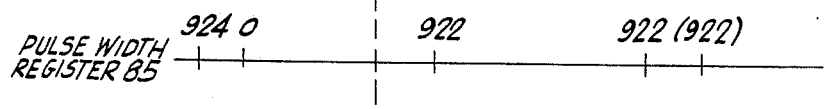
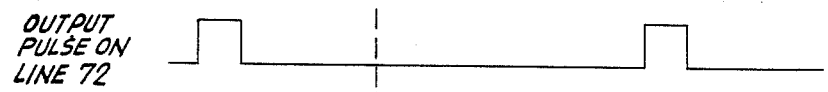
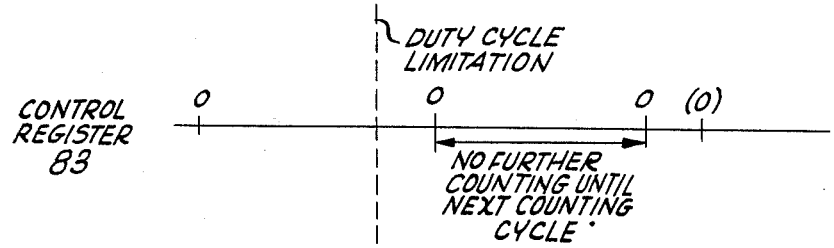
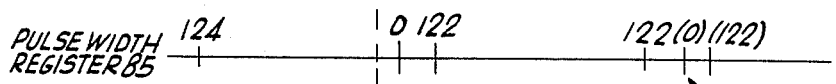
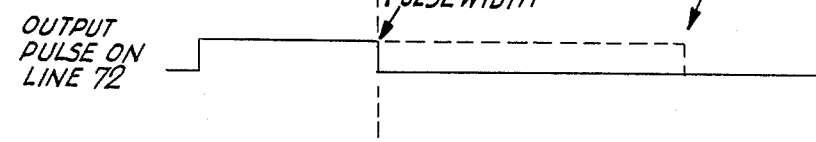

fig.6a

| COUNT STATE OF CONTROL REGISTER 83 | COUNT STATE OF PULSE WIDTH REGISTER 85 | STATE OF FLIP-FLOP 119 FALSE=0=RESET TRUE=1=SET | STATE OF FLIP-FLOP 118 FALSE=0=RESET TRUE=1=SET |
|---|---|---|---|
| 0 | 18 | 0 | 1 |
| 1 | 18 | 0 | 1 |
| 2 | 18 | 0 | 1 |
| 3 | 19 | 0 | 1 |
| 4 | 20 | 0 | 1 |
| ↓ | ↓ | ↓ | ↓ |
| 495 | 511 | 0 | 1 |
| 496 | 512 | 0 | 1 |
| 497 | 513 | 1 | 1 |
| 498 | 514 | 1 | 0 |
| ↓ | ↓ | ↓ | ↓ |
| 1007 | 1023 | 1 | 0 |
| 1008 | 0 | 1 | 0 |
| 1008 | 1 | 1 | 0 |
| 1008 | 2 | 1 | 0 |
| 1008 | 3 | 1 | 0 |
| ↓ | ↓ | ↓ | ↓ |
| 1008 | 19 | 1 | 0 |
| 1008 | 20 | 1 | 0 |
| 1008 | 21 | 0 | 0 |
| 1009 | 22 | 0 | 0 |
| ↓ | ↓ | ↓ | ↓ |
| 1022 | 35 | 0 | 0 |
| 1023 | 36 | 0 | 0 |
| 0 | 37 | 0 | 0 | fig.6b

| COUNT STATE OF CONTROL REGISTER 83 | COUNT STATE OF PULSE WIDTH REGISTER 85 | STATE OF FLIP-FLOP 119 FALSE=0=RESET TRUE=1=SET | STATE OF FLIP-FLOP 118 FALSE=0=RESET TRUE=1=SET |
|---|---|---|---|
| 0 | 512 | 1 | 0 |
| 1 | 512 | 1 | 0 |
| 2 | 512 | 1 | 0 |
| 3 | 513 | 1 | 0 |
| 4 | 514 | 1 | 0 |
| ↓ | ↓ | ↓ | ↓ |
| 513 | 1023 | 1 | 0 |
| 514 | 0 | 1 | 0 |
| 514 | 1 | 1 | 0 |
| ↓ | ↓ | ↓ | ↓ |
| 514 | 19 | 1 | 0 |
| 514 | 20 | 1 | 0 |
| 514 | 21 | 0 | 0 |
| 515 | 22 | 0 | 0 |
| ↓ | ↓ | ↓ | ↓ |
| 1023 | 530 | 0 | 0 |
| 0 | 531 | 0 | 0 | fig.6e

| COUNT STATE OF CONTROL REGISTER 83 | COUNT STATE OF PULSE WIDTH REGISTER 85 | STATE OF FLIP-FLOP 119 FALSE = 0 = RESET TRUE = 1 = SET | STATE OF FLIP-FLOP 118 FALSE = 0 = RESET TRUE = 1 = SET |
|---|---|---|---|
| 1 | 512 | 0 | 1 |
| 2 | 512 | 1 | 1 |
| 3 | 513 | 1 | 0 |
| ↓ | ↓ | ↓ | ↓ |
| 513 | 1023 | 1 | 0 |
| 514 | 0 | 1 | 0 |
| 514 | 1 | 1 | 0 |
| ↓ | ↓ | ↓ | ↓ |
| 514 | 20 | 1 | 0 |
| 514 | 21 | 0 | 0 |
| 515 | 22 | 0 | 0 |
| ↓ | ↓ | ↓ | ↓ |
| 1023 | 530 | 0 | 0 |
| 0 | 531 | 0 | 0 | fig.6f

| COUNT STATE OF CONTROL REGISTER 83 | COUNT STATE OF PULSE WIDTH REGISTER 85 | STATE OF FLIP-FLOP 119 FALSE = 0 = RESET TRUE = 1 = SET | STATE OF FLIP-FLOP 118 FALSE = 0 = RESET TRUE = 1 = SET |
|---|---|---|---|
| 500 | 15 | 0 | 1 |
| 501 | 16 | 0 | 1 |
| ↓ | ↓ | ↓ | ↓ |
| 997 | 512 | 0 | 1 |
| 998 | 513 | 1 | 1 |
| 999 | 514 | 1 | 0 |
| ↓ | ↓ | ↓ | ↓ |
| 1023 | 538 | 1 | 0 |
| 0 | 539 | 1 | 0 |
| 1 | 539 | 1 | 0 |
| 2 | 539 | 1 | 0 |
| 3 | 540 | 1 | 0 |
| 4 | 541 | 1 | 0 |
| ↓ | ↓ | ↓ | ↓ |
| 486 | 1023 | 1 | 0 |
| 487 | 0 | 1 | 0 |
| 487 | 1 | 1 | 0 |
| ↓ | ↓ | ↓ | ↓ |
| 487 | 19 | 1 | 0 |
| 487 | 20 | 1 | 0 |
| 487 | 21 | 0 | 0 |
| 488 | 22 | 0 | 0 |
| ↓ | ↓ | ↓ | ↓ |
| 1023 | 557 | 0 | 0 |
| 0 | 558 | 0 | 0 |

DRZ PULSE INITIATES NEXT COUNTING CYCLE fig.6c

| COUNT STATE OF CONTROL REGISTER 83 | COUNT STATE OF PULSE WIDTH REGISTER 85 | STATE OF FLIP-FLOP 119 FALSE = 0 = RESET TRUE = 1 = SET | STATE OF FLIP-FLOP 118 FALSE = 0 = RESET TRUE = 1 = SET |
|---|---|---|---|
| 0 | 1023 | 1 | 0 |
| 1 | 1023 | 1 | 0 |
| 2 | 1023 | 1 | 0 |
| 3 | 0 | 1 | 0 |
| 3 | 1 | 1 | 0 |
| 3 | 2 | 1 | 0 |
| ↓ | ↓ | ↓ | ↓ |
| 3 | 20 | 1 | 0 |
| 3 | 21 | 0 | 0 |
| 4 | 22 | 0 | 0 |
| ↓ | ↓ | ↓ | ↓ |
| 1005 | 1023 | 0 | 0 |
| 1006 | 0 | 0 | 0 |
| ↓ | ↓ | ↓ | ↓ |
| 1023 | 17 | 0 | 0 |
| 0 | 18 | 0 | 0 | fig.6d

| COUNT STATE OF CONTROL REGISTER 83 | COUNT STATE OF PULSE WIDTH REGISTER 85 | STATE OF FLIP-FLOP 119 FALSE = 0 = RESET TRUE = 1 = SET | STATE OF FLIP-FLOP 118 FALSE = 0 = RESET TRUE = 1 = SET |
|---|---|---|---|
| 1 | 18 | 0 | 1 |
| 2 | 18 | 0 | 1 |
| 3 | 19 | 0 | 1 |
| 4 | 20 | 0 | 1 |
| ↓ | ↓ | ↓ | ↓ |
| 495 | 511 | 0 | 1 |
| 496 | 512 | 0 | 1 |
| 497 | 513 | 1 | 1 |
| 498 | 514 | 1 | 0 |
| ↓ | ↓ | ↓ | ↓ |
| 1007 | 1023 | 1 | 0 |
| 1008 | 0 | 1 | 0 |
| 1008 | 1 | 1 | 0 |
| 1008 | 2 | 1 | 0 |
| 1008 | 3 | 1 | 0 |
| ↓ | ↓ | ↓ | ↓ |
| 1008 | 19 | 1 | 0 |
| 1008 | 20 | 1 | 0 |
| 1008 | 21 | 0 | 0 |
| 1009 | 22 | 0 | 0 |
| ↓ | ↓ | ↓ | ↓ |
| 1022 | 35 | 0 | 0 |
| 1023 | 36 | 0 | 0 |
| 0 | 37 | 0 | 0 | fig.6g

| | COUNT STATE OF CONTROL REGISTER 83 | COUNT STATE OF PULSE WIDTH REGISTER 85 | STATE OF FLIP-FLOP 119 FALSE = 0 = RESET TRUE = 1 = SET | STATE OF FLIP-FLOP 118 FALSE = 0 = RESET TRUE = 1 = SET |
|---|---|---|---|---|
| | 600 | 15 | 0 | 1 |
| | 601 | 16 | 0 | 1 |
| | ↓ | ↓ | ↓ | ↓ |
| DRZ PULSE INITIATES NEXT COUNTING CYCLE → | 1023 | 438 | 0 | 1 |
| | 0 | 439 | 0 | 1 |
| | ↓ | ↓ | ↓ | ↓ |
| | 1 | 439 | 0 | 1 |
| | 2 | 439 | 0 | 1 |
| | 3 | 440 | 0 | 1 |
| | 4 | 441 | 0 | 1 |
| | ↓ | ↓ | ↓ | ↓ |
| | 74 | 511 | 0 | 1 |
| | 75 | 512 | 0 | 1 |
| | 76 | 513 | 1 | 1 |
| | 77 | 514 | 1 | 0 |
| | ↓ | ↓ | ↓ | ↓ |
| | 586 | 1023 | 1 | 0 |
| | 587 | 0 | 1 | 0 |
| | 587 | 1 | 1 | 0 |
| | 587 | 2 | 1 | 0 |
| | 587 | 3 | 1 | 0 |
| | ↓ | ↓ | ↓ | ↓ |
| | 587 | 19 | 1 | 0 |
| | 587 | 20 | 1 | 0 |
| | 587 | 21 | 0 | 0 |
| | 588 | 22 | 0 | 0 |
| | ↓ | ↓ | ↓ | ↓ |
| | 1022 | 456 | 0 | 0 |
| | 1023 | 457 | 0 | 0 |
| | 0 | 458 | 0 | 0 |

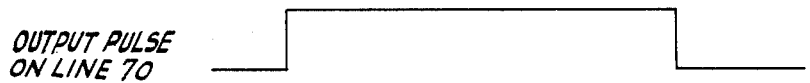
Fig. 7a — OUTPUT PULSE ON LINE 70
Fig. 7b — MOTOR DRIVE PULSES GENERATED
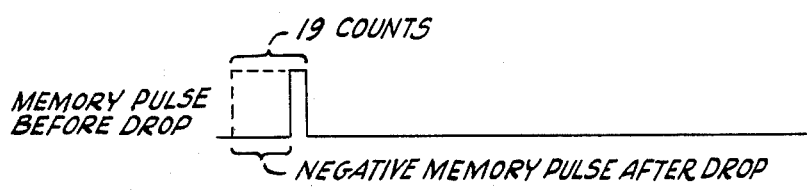
Fig. 8a — MEMORY PULSE BEFORE DROP (19 COUNTS; NEGATIVE MEMORY PULSE AFTER DROP)
Fig. 8b — MOTOR DRIVE PULSE GENERATED (NO DELAY)
Fig. 8c — MEMORY PULSE AFTER DROP
Fig. 8d — NO MOTOR PULSES (GATED OFF)
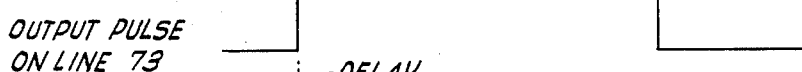
Fig. 9a — OUTPUT PULSE ON LINE 73 (DELAY)
Fig. 9b — CONTROLLER MECHANISM RESPONSE
Fig. 10a — NARROW MEMORY PULSE
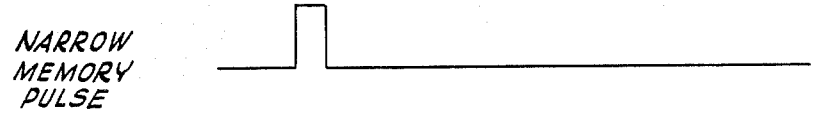
Fig. 10b — MECHANISM (NO OUTPUT)

METHOD AND APPARATUS FOR FLUID FLOW CONTROL

BACKGROUND OF THE INVENTION

This invention relates generally to improvements in fluid flow control systems and, more particularly, to a new and improved automatic, self-regulating, highly accurate drop flow control system for parenteral administration of medical fluids over a wide range of fluid flow rates and capable of utilizing a variety of different electromechanical output devices, such as positive pressure infusion pumps using stepping motors or the like, as well as controllers using electrically actuated I.V. tube pinchers.

The usual medical procedure for the gradual parenteral administration of liquids into the human body, such as liquid nutrients, blood or plasma, makes use of apparatus which is commonly referred to in the medical art as an intravenous administration set. The intravenous set usually comprises a bottle of liquid, normally supported in an inverted position, an intravenous feeding tube, typically of clear plastic, and a suitable valve mechanism, such as a roll clamp, which allows the liquid to drip out of the bottle at a selectively adjustable rate into a transparent drip chamber below the bottle. The drip chamber serves the dual function of allowing a nurse or other attendant to observe the rate at which the liquid drips out of the bottle and also creates a reservoir for the liquid at the lower end of the drip chamber to insure that no air enters the main feeding tube leading to the patient.

While observation of the rate of drop flow via the drip chamber is a simple way of controlling the amount of liquid fed to a patient over a period of time, its ultimate effectiveness requires that a relatively constant vigil be maintained on the drop flow, lest it cease entirely due to exhaustion of the liquid supply or become a continuous stream and perhaps increase the rate of liquid introduction to the patient to dangerous levels.

By way of example, it has been the general practice in hospitals to have nurses periodically monitor drop flow rate at each intravenous feeding or parenteral infusion station. Such monitoring of drop flow is a tedious and time consuming process, prone to error and associated, possible serious consequences, and resulting in a substantial reduction of the available time of qualified medical personnel for other important duties. Typically, the nurse monitoring drop flow rate will use a watch to time the number of drops flowing in an interval of one or more minutes, and she will then mentally perform the mathematics necessary to convert the observed data to an appropriate fluid flow rate, e.g., in cubic centimeters per hour or drops per minute. If the calculated flow rate is substantially different than the prescribed rate, the nurse must manually adjust the roll clamp for a new rate, count drops again, and recalculate to measure the new rate.

Obviously, each of the aforedescribed measurements and calculations and flow rate adjustments usually take several minutes time which, when multiplied by the number of stations being monitored and the number of times each station should be monitored per day, can result in a substantial percentage of total personnel time available. In addition, under the pressure of a heavy schedule, the observations and calculations performed by a harried nurse in measuring and adjusting flow rate may not always prove to be reliable and, hence, errors do occur resulting in undesired, possibly dangerous infusion flow rates.

In addition to the aforedescribed difficulties, the parenteral administration of medical liquids by gravity induced hydrostatic pressure infusion of the liquid from a bottle or other container suspended above a patient, is very susceptible to fluid flow rate variation due to changes in the liquid level in the bottle, changes in temperature, changes in the venous or arterial pressure of the patient, patient movement, and drift in the effective setting of the roll clamp or other valve mechanism pinching the feeding tube. Moreover, there are a number of situations, such as in intensive care, cardiac and pediatric patients, or where rather potent drugs are being administered, where the desired drop flow rate must be capable of precise selection and must not drift beyond certain prescribed limits. In addition, it is extremely important in such situations for medical personnel to be informed of undesired fluctuations in flow rate, failure of the fluid delivery system, or exhaustion of liquid supply when the bottle is emptied.

It will be apparent, therefore, that some of the most critical problems confronting hospital personnel faced with an overwhelming duty schedule and limited time availability are the problems of quickly, easily, reliably and accurately monitoring and regulating drop flow rate in the parenteral administration of medical liquids.

In recent years, a number of electrical monitoring systems, drop flow controllers and infusion pumps have been developed to accomplish the various tasks of sensing and regulating drop flow rates. Some of these devices have also been capable of activating alarms when a potentially dangerous condition exists, thus freeing medical personnel to some extent for other duties. However, while such monitoring and drop rate control devices have generally served their purpose, they have not always proven entirely satisfactory from the standpoint of cost, complexity, stability, reliability, accuracy, adaptability to different types of electromechanical output devices, or precision of adjustment over a wide range of selected flow rates. In addition, such systems have sometimes been subject to drift and substantial flow rate variations due to changes in temperature, feeding tube crimps, variations in venous or arterial pressure of the patient, or variations in the height of the bottle or solution level within the bottle. Substantial difficulties have been experienced particularly in connection with establishing and maintaining such accurate drop flow at very low flow rates.

Hence, those concerned with the development and use of parenteral fluid administration systems, and particularly those concerned with the design of automatic fluid flow control systems, have long recognized the need for improved, relatively simple, economical, adaptable, reliable, stable and accurate devices for fluid flow control which obviates the aforedescribed difficulties. The present invention clearly fulfills this need.

SUMMARY OF THE INVENTION

Briefly, and in general terms, the present invention provides a new and improved method and apparatus for controlling drop flow in the parenteral administration of medical liquids, wherein the frequency and pulse width of electrical output control pulses which operate an electromechanical output control device regulating liquid flow in a feeding tube are controlled by a unique digital system capable of sensing and regulating drop flow rate very accurately over a wide range of flow rates and with a variety of different electromechanical output devices.

The system for establishing the frequency of the output pulses to the electromechanical control device regulating fluid flow is an open loop digital command system embodying an all digital pulse generation and rate selection subsystem wherein the output pulse frequency representing desired drop flow rate is a relatively high, preferably non-integral multiple of the actual drop flow rate frequency. In the case of some electromechanical output control devices, as reciprocating I.V. tube pinchers, such a relationship between the commanded output pulse frequency and the desired drop rate frequency tends to produce less drop distortion and more consistently repeatable drop size from one drop to another.

Additional control over drop flow rate is accomplished by varying the pulse width of the output electrical pulses to the electromechanical control device, i.e., the time duration of the period of energization of the output control device provided by the output pulse. This output pulse width is precisely controlled by a closed loop digital system which varies the pulse width in digital servo fashion to establish the desired drop flow rate while maintaining the aforedescribed relationship between the commanded output pulse frequency and the desired drop flow rate frequency.

The width of the electrical output pulses to the electromechanical control device is uniquely determined by a digital memory subsystem which includes a pair of counters, one counter embodying a scanning control register, the other counter embodying a pulse width register. The scanning control register determines the duration of each counting cycle for itself and the pulse width register, by initiating and terminating the counting cycle for both registers, the normal rest state for the scanning register between counting cycles (i.e., the initial and final state for each counting (cycle) being its "zero" state.

Initiation of each counting cycle, and each output electrical pulse from the overall control system, occurs with each pulse generated by the open loop pulse generation and rate selection subsystem. Each output pulse is terminated whenever the pulse width register is counted to its "zero" state. The count in the pulse width register at the termination of each counting cycle is a measure of the pulse width for the electrical output pulse to be generated by the digital system on the next succeeding counting cycle. In this regard, the pulse width of the output pulse, expressed as a function of the content of the pulse width register is determined by the number of counts required to count up the pulse width register from its initial count state (which is the last count state in the immediately preceding counting cycle) to its "zero" state, the output pulse being terminated as the pulse width register is counted through "zero".

The pulse width register comes to rest in each counting cycle at a count which determines the pulse width for the next output pulse to be generated, each counting cycle being terminated when the scanning control register has counted to "zero ". Hence, a unique pulse width digital memory is provided by the present invention.

In accordance with the invention, the pulse width register is uniformly decremented by a predetermined number of counts relative to the scanning control register during each counting cycle, to provide output electrical pulses of gradually increasing pulse width. The pulse width register is also incremented a prescribed number of counts relative to the scanning control register, each time a drop is detected by the system, thereby narrowing the pulse width whenever a drop is detected. The ratio of the number of counts by which the pulse width register is incremented each time a drop is detected, to the number of counts the pulse width register is decremented during each counting cycle, is the same as the aforedescribed ratio of output pulse frequency to desired drop flow rate frequency. Hence, the desired frequency relationship is precisely established with digital precision.

A duty cycle limitation subsystem overrides the pulse width determination by the digital memory subsystem in the event the pulse width prescribed by the memory subsystem would exceed an appropriate maximum duty cycle suited to the particular electromechanical output control device being utilized, in order to avoid the possibility of inducing runaway free flow conditions, due to mechanical limitations in the output control device, and consequent loss of control.

The duty cycle limitation subsystem monitors the commanded period between successive initiations of electrical output pulses and, at the desired duty cycle limitation point selected for the particular electromechanical output control device being utilized, terminates the output pulse, providing an instantaneous limitation on the electrical output to the mechanical subsystem, while simultaneously speeding up the counting rate to the digital memory so that the counting cycle is completed more rapidly. This latter feature also insures that the digital memory will always have completed the last counting cycle prior to initiation of the next counting cycle, in the event a high pulse frequency is commanded with a period between initiation of output pulses shorter than the counting cycle of the memory at the normal counting rate. However, the accelerated counting rate to the digital memory provided by the duty cycle limitation subsystem insures completion of each counting cycle even at the highest selected output pulse rates.

A start-up subsystem, effective only during initial operation of the system or after coming out of an alarm state, temporarily controls the rate selection and memory subsystems and accelerates initial pulse width regulation to more rapidly achieve normal operating conditions. In this connection, the pulse width register is decremented by a greater number of counts per counting cycle during the start-up phase to increase the width of the electrical output pulses more rapidly. In addition, and only during the start-up phase, the rate selection subsystem is present internally to a prescribed rate, to insure that the output pulses are not coming too slowly or too rapidly during initial adjustment of the overall system. The start-up phase continues until a prescribed number of initial drops have been detected, at which time the start-up subsystem relinquishes control, and normal pulse rate control and output pulse width adjustment occurs for subsequent drop flow beyond the initial few drops detected.

For certain types of electromechanical output control devices, particularly those capable of functioning properly with very narrow pulse width input, the system of the present invention is capable of functioning normally on an expanded low level operational basis, without going into alarm, by storing and processing the equivalent of negative pulse width in the digital memory. This condition may occur with normal low level operation in which extremely narrow pulse widths are generated, so that further incrementing of the pulse width register upon detection of drops causes the pulse width register to overflow.

Overflow of the pulse width register countwise is equivalent to underflow of pulse width, i.e., negative pulse width, which is manifested by the sudden transition from a very narrow output pulse (a high count in the pulse width register) to a very wide output pulse (a very low count in the pulse width register). Assuming the system is operating to provide normal fluid flow, i.e., there are no flow conditions warranting generation of an alarm state, the negative pulse width condition will be only transitory, and successive decrementing of the pulse width register in succeeding counting cycles should bring the digital memory out of the negative pulse width region and restore normal narrow output pulse generation. Hence, the capability of operation in the negative pulse width region by the system of the present invention enables an expanded dynamic range of operation without the need for expanding the count capacity of the digital memory.

The electromechanical output control devices which may be utilized with the system of the present invention generally fall into one of two categories, positive pressure infusion devices such as pumps, or devices which simply open and close a feeding tube and are dependent upon gravity induced hydrostatic pressure for producing drop flow. The latter category includes I.V. tube pincher devices wherein a feeding tube clamping member, normally in the tube shut-off position, is repeatedly moved to the tube-open position by a suitable electromechanical driver which is, in turn, energized by the electrical output pulses from the previously described digital system.

Since gravity induced hydrostatic pressure is a function of such parameters as the height of the bottle, the liquid level in the bottle, and the size and flexibility of the feeding tube, and each of these parameters can be altered, it is desirable to visually observe an indication of the output pulse width operating range so that, in the event pulse width is not in the optimum range, suitable adjustments can be made, such as raising or lowering the height of the bottle, to establish hydrostatic pressure levels in the feeding tube appropriate to pulse generation in the optimum region of operation. The present system provides such a visual indication by monitoring the status of the pulse width register and indicating, by means of a pair of lights, whether the electrical output pulses being generated by the system fall within the high, low or optimum pulse width ranges.

The digital memory status is also monitored so that out-of-limit conditions calling for flow rates in excess of system delivery capability, or indicating a leakage flow rate which cannot be terminated by the output control device, trigger appropriate alarm subsystems. The system provides the flexibility of a high level alarm which indicates a demand for too wide an output pulse, a variety of low level alarms responsive to specified non-tolerated sequences of pulse widths, including excessive negative pulse widths for certain types of output control devices.

In addition, in order to warn appropriate medical personnel of an exhausted liquid supply or any other condition in the administration set preventing fluid delivery, the alarm subsystem is responsive to a lack of drop flow detected in a predetermined period of time and as a function of a predetermined number of electrical events in the control system. In this regard, the system alarms if no drops are detected after a prescribed number of output pulses have been commanded by the open loop pulse generation subsystem, and the system will also alarm if no drops or output electrical pulses have occured in a prescribed time interval.

The new and improved fluid flow control system of the present invention is extremely accurate, reliable and easy to use. The system provides enhanced digital precision in selecting and maintaining drop flow rates throughout a wide range, and the system is quick to inform medical personnel of any conditions which might pose a hazard to the patient. Hence, the system of the present invention minimizes the time consuming and error prone aspects of human monitoring and flow rate adjustment and provides substantial improvement in economy, adaptability to a variety of different mechanical output control devices, reliability, stability and accuracy over previous automatic control systems.

These and other objects and advantages of the invention will become apparent from the following more detailed description, when taken in conjunction with the accompanying drawings of illustrative embodiments.

DESCRIPTION OF THE DRAWINGS

FIGS. 4a, 4b and 4c are combined block diagrams and electrical schematics of one embodiment of an overall fluid flow control system in accordance with the present invention, FIG. 4a being primarily directed to the input and timing subsystem and the output subsystem, FIG. 4b being primarily directed to the memory and control subsystems, FIG. 4c being primarily directed to the visual pulse width monitoring subsystem and alarm subsystem;

FIGS. 5a–5h are graphical representations illustrating various electrical states in the overall control system of FIGS. 4a, 4b and 4c for a variety of conditions of operation which demonstrate the functioning of the duty cycle limitation subsystem;

FIGS. 6a–6g are tables illustrating register and flip-flop states in the overall system of FIGS. 4a–4c for a variety of different conditions under which drops may be detected;

FIGS. 7a and 7b and FIGS. 8a–8d are waveforms for various portions of the overall system of FIGS. 4a–4c when the system is being operated in the pump mode; and FIGS. 9a, 9b, 10a and 10b are waveforms for various portions of the overall system of FIGS. 4a–4c when the system is being operated in the controller mode.

DESCRIPTION OF THE PREFERRED EMBODIMENT

Figure 1:
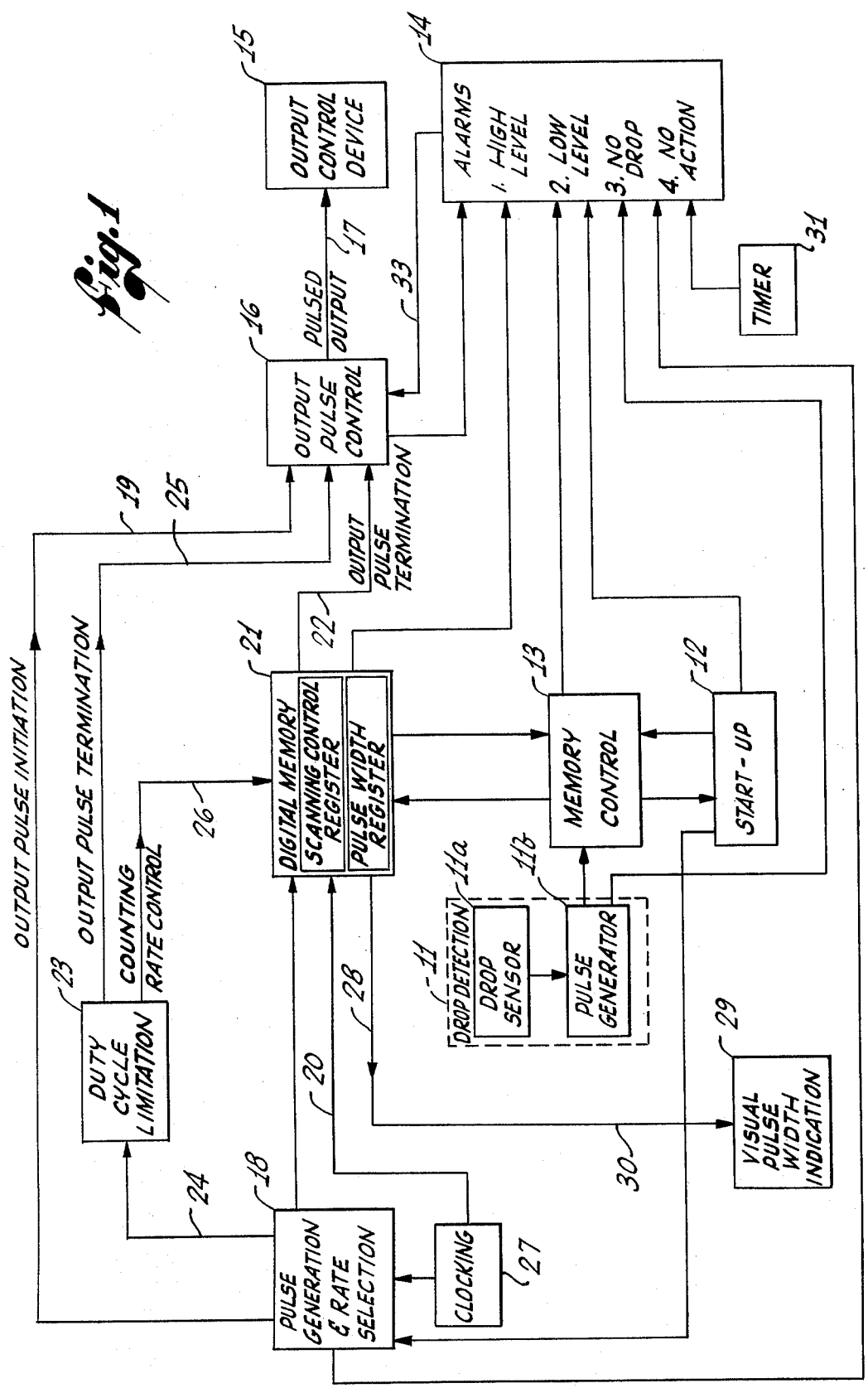
FIG. 1 is a block diagram of an overall system in which some of the basic concepts of the fluid flow control system of the present invention are embodied.

Referring now to FIG. 1 of the drawings, there is shown a new and improved system for fluid flow control embodying features of the present invention. In the ensuing description, while reference will be made to the term "I.V." normally connoting intravenous administration, it is to be understood that this is by way of example only, and the flow control system of the present invention is suitable for other forms of parenteral administration as well as intravenous administration.

In order to control drop flow rate, it is necessary to continuously monitor the actual drop flow as it occurs in an I.V. administration set. This is accomplished in the system of FIG. 1 by a drop detection subsystem 11 which includes a drop sensor 11a and a pulse generator 11b, both well known in the art, adapted to detect each drop as it falls and generate electrical pulses at a frequency equal to the drop flow rate.

The drop sensor 11a monitors drop flow in a drip chamber (not shown) of the I.V. administration set and typically may include a sensor housing (not shown) containing a reference light source located a fixed distance from a photocell to define an optical sensing gap therebetween, with a reference light beam normally impinging upon the photocell. The housing is appropriately clamped upon the drip chamber of the I.V. set, with the transparent drip chamber positioned within the sensing gap to intercept the reference beam. A falling drop of liquid within the drip chamber interrupts the reference beam, and the variation in electrical response of the photocell is directed to appropriate circuitry indicating the presence of a drop. One example of a suitable drop sensor 11a is set forth in U.S. Pat. No. 3,596,515, invention, Richard A. Cramer. While a photocell monitoring device is ideally suited for the drop sensor 11a, it will be appreciated that any drop sensing device capable of providing an electrical indication of the detection of a drop may be used without departing from the spirit and scope of the invention.

The pulse generator 11b is typically a conventional monostable flip-flop (one-shot) which provides an output pulse each time a drop is detected by the drop sensor 11a, the output pulses having a prescribed pulse width and amplitude compatible with the input circuit requirements of the particular monitoring and control system utilized. The pulse output from the pulse generator 11b, representing the detected drop flow rate, is directed as one input to a memory control subsystem 13, and is also directed as input to an alarm subsystem 14.

Fluid flow in the feeding tube of the I.V. administration set is regulated by the system of the present invention via an electromechanical output control device 15 which, in turn, is periodically energized by receiving as electrical input the pulsed output over line 17 from an output pulse control subsystem 16.

A variety of different electromechanical output control devices 15 can be used with the system of the present invention, such as positive pressure infusion pumps, driven by a d.c. stepping motor, or other types of a.c. or d.c. motors, or devices which simply open and close a feeding tube and are dependent upon gravity induced hydrostatic pressure for drop flow, i.e., a drop flow controller rather than a pump. By way of example, the system of the present invention is described in connection with the operation of two different types of output control devices, one from each of the aforedescribed categories.

In the infusion pump category, a d.c. stepping motor is employed as a drive for the infusion pump to provide a stepped incremental mechanical output to a plurality of cam followers or the like (not shown) which massage the I.V. feeding tube and generate a peristaltic pump action capable of developing a substantial positive pressure in the feeding tube.

In the flow controller category, the controller includes an I.V. tube pincher device wherein a feeding tube clamping member, normally spring biased to the tube shut-off position, is repetitively moved to the tube-open position by a suitable electromagnetic driver which is, in turn, energized by the electrical output pulses over line 17 from the pulse control subsystem 16. Each output pulse directed to the output control device 15, in the case of the controller, causes the clamping member to be retracted and thereby opens the feeding tube for the duration of the output energizing pulse width. By way of example, the I.V. controller output control device 15 may be type set forth in U.S. Pat. No. 3,756,556, inventor, Heinz W. Georgi.

In the case of the stepping motor infusion pump, each electrical output pulse over line 17 from the pulse control subsystem 16 gates on a burst of stepping motor driver pulses, the duration of the driver pulse burst substantially matching the duration of the output energizing pulse width. Each driver pulse steps the motor a precisely defined rotational increment and thereby peristaltically induces fluid flow in the feeding tube by advancing a body of fluid trapped between the cam followers.

While the invention is described in detail, by way of illustration, in connection with the aforementioned stepping motor infusion pump and I.V. controller as typical output control devices 15, it will be appreciated that other output control devices can be readily utilized within the framework of the system described, without departing from the spirit and scope of the invention.

A pulse generation and rate selection subsystem 18, which is an open digital subsystem, establishes the frequency of the output pulses produced by the system over line 17 to the output control device 15. The subsystem 18 is an all digital pulse generation subsystem which generates a pulse frequency output over line 19 to the output pulse control subsystem 16 and directs the same output over line 19 to a digital memory subsystem 21.

Figure 2:
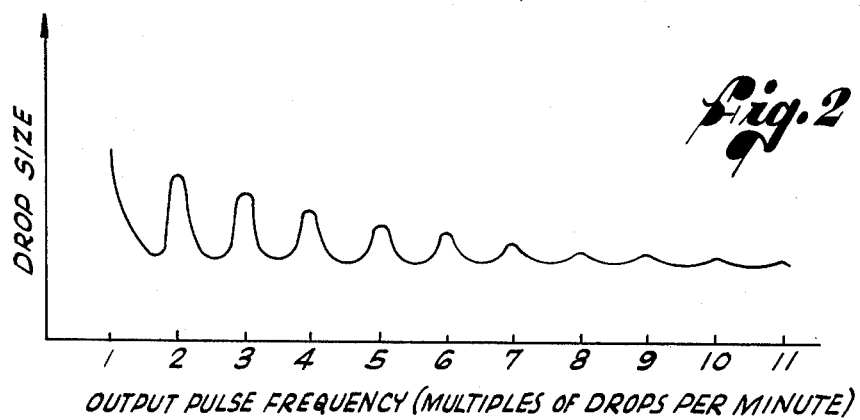
FIG. 2 is a graphical representation illustrating typical drop size as a function of output pulse frequency.

The desired drop flow rate is selected by the operator through adjustment of the pulse generation and rate selection subsystem 18. The output pulse frequency from the subsystem 18 is, in accordance with the invention, not the actual drop flow rate desire, but rather a relatively high, preferably non-integral multiple of the actual drop flow rate frequency, e.g., typically a ratio of 10-In the case of some electromechanical output control devices 15, such as reciprocating I.V. tube pinchers, such a relationship between the commanded output pulse frequency and the desired drop rate frequency tends to produce less drop distortion and more consistently repeatable drop size from one drop to another. This is apparent from FIG. 2 of the drawings which illustrates typical drop size as a function of output pulse frequency using I.V. controller. The basic concept of using such a high, non-integral ratio of output pulse frequency to desired drop flow rate frequency with I.V. controllers has been previously set forth in U.S. Pat. No. 3,800,794, issued Apr. 2, 1974, to the same inventor as the present application. However, an analog memory and different type of control subsystem is taught in the aforementioned U.S. Pat. No. 3,800,794 than in the present application.

The command pulses generated over line 19 to the output pulse control subsystem 16 determine the initiation of each output pulse over line 17 to the output control device 15, whereas the termination of each output pulse is determined by the digital memory subsystem 21 which directs an input over line 22 to the pulse control subsystem 16. Hence, in addition to the output pulse frequency control provided by the pulse generation and rate selection subsystem 18, additional control over drop flow rate is accomplished by varying the pulse width of the output electrical pulses to the control device 15, i.e., the time duration of the period of energization of the output control device provided by each electrical output on line 17. The output pulse width is precisely controlled by a closed loop digital subsystem, which includes the digital memory subsystem 21, and which varies the pulse width in digital servo fashion to establish the desired drop flow rate while always maintaining the aforedescribed relationship between the commanded output pulse frequency and the desired drop flow rate.

The width of the electrical output pulses to the output control device 15 is uniquely determined in the system of the present invention by the digital memory subsystem 21 in conjuction with the memory control subsystem 13, which, in turn, receives information not only from the digital memory subsystem but also from the drop detection subsystem 11 which includes the drop sensor 11a and pulse generator 11b.

The digital memory subsystem 21 includes a pair of digital counters, one counter embodying a scanning control register, the other counter embodying a pulse width register. These register undergo a counting cycle which is initiated each time a pulse is generated over line 20 by the pulse generation and rate selection subsystem 18, and each counting cycle must be completed before the next pulse is produced on line 20. The scanning control register determines the duration of each counting cycle, for itself and for the pulse width register, by initiating and terminating the counting cycle for both registers, the normal rest state for the scanning register between counting cycles (i.e., the initial and final state for each counting cycle) being its "zero" state.

As previously indicated, not only is initiation of each counting cycle determined, but each output electrical pulse from the system over line 17 is also initiated, with each pulse generated by the open loop pulse generation and rate selection subsystem 18. Each output pulse over line 17 to the control device 15 is terminated whenever the pulse width register of the memory subsystem 21 is counted to its "zero" state.

The final count in the pulse width register at the termination of each counting cycle is a measure of the pulse width for the next electrical output to be generated by the system over line 17 on the next succeeding counting cycle. In this regard, the pulse width of the output pulse over line 17 to the control device 15, expressed as a function of the pulse width register count, is determined by the number of counts required to count up the pulse width register from its initial count state (which is the final count state in the immediately preceeding counting cycle) to its "zero" state, the output energizing pulse to the control device 15 being terminated as the pulse width register is counted through zero. The latter state is communicated over line 22 to the output pulse control subsystem 16.

The pulse width register comes to rest in each counting cycle at a final count which determines the pulse width for the next output pulse to be generated over line 17, each counting cycle being terminated whe the scanning control register has counted to its "zero" state. In accordance with the invention, the pulse width register in the digital memory subsystem 21 is uniformly decremented by a predetermined number of counts relative to the scanning control register during each counting cycle, to provide output electrical pulses of gradually increasing pulse width. The pulse width register is also incremented a prescribed number of counts relative to the scanning control register each time a drop is detected by the drop sensor 11, thereby narrowing the pulse width whenever a drop is detected. This is accomplished via the memory control subsystem 13.

The ratio of th number of counts by which the pulse width register is incremented each time a drop is detected, to the number of counts the pulse width register is decremented during each counting cycle, is the same as the aforedescribed ratio of commanded output pulse frequency to desired drop flow rate frequency. By way of example, in a presently preferred embodiment of the system of the present invention, the pulse width register is decremented by 2 counts during each counting cycle and incremented by 21 counts each time a drop is detected by the drop sensor 11a. Hence, the desired input to output frequency ratio of 10-½ is precisely established in the digital memory subsystem 21.

Figure 3:
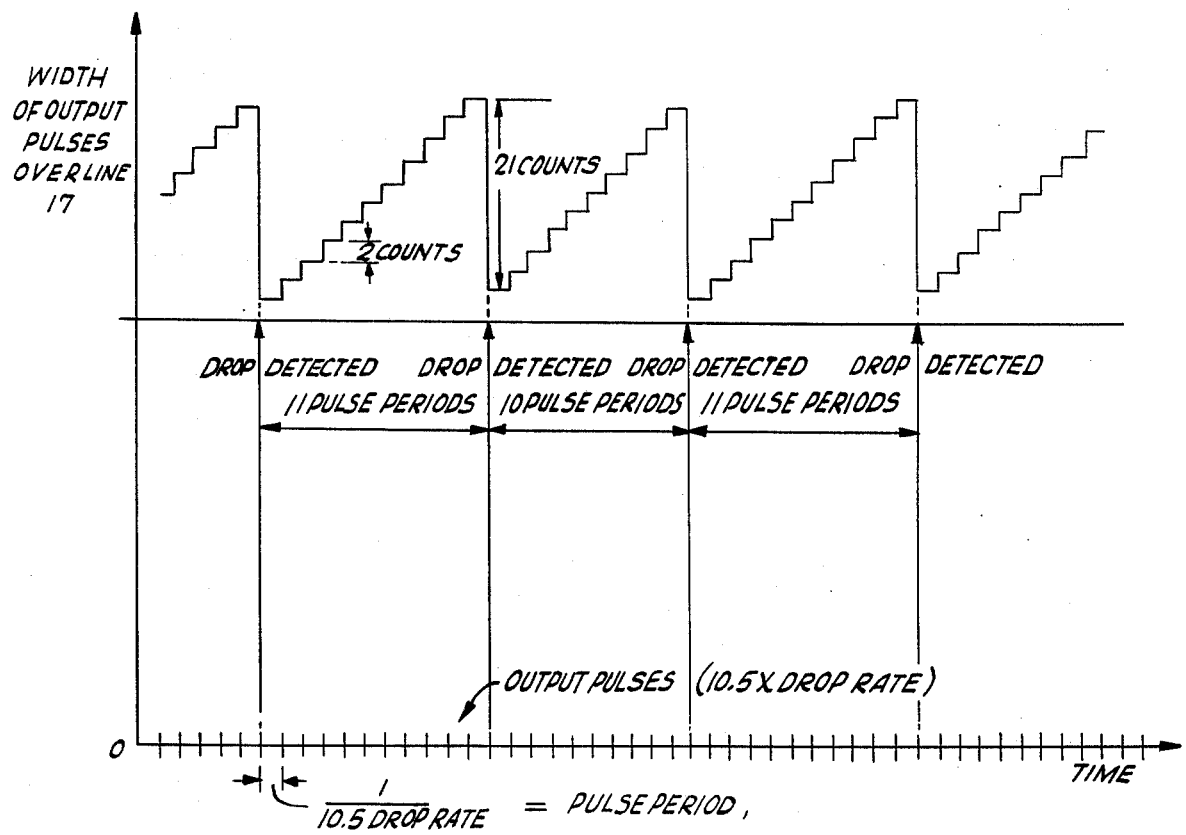
FIG. 3 is a graphical representation of output pulse width as a function of time.

The manner in which the output pulse width over line 17, indicated in terms of the counts stored in the pulse width register of the memory subsystem 21, varies as a function of time is illustrated in FIG. 3 of the drawings. It will be apparent from FIG. 3 that the output pulse width varies as a staircase function, with each increase in pulse width being 2 counts decremented from the pulse width register and each decrease in pulse width being 21 counts incremented into the pulse width register at the point of drop detection.

The width of each step in the staircase waveform is a time period which is the reciprocal of the output pulse frequency on line 17, or 1/10-½ × drop rate. It will be noted that each staircase pattern between successive drop detection events varies in the number of pulse periods or steps included, the patterns alternating in 10 and 11 pulse period groupings to provide an average interval between successive drop detections of 10-½ pulse periods, the desired ratio.

A start-up subsystem 12 is effective during initial start-up of the overall system, as well as each time the system is brought out of an alarm state. In this regard, the system starts out with both of the registers of the digital memory subsystem 21 reset to their "zero" states, so that normal operation of the system would produce extremely narrow initial output pulses over line 17.

The start-up subsystem alters the normal operation of the memory control subsystem 13 by accelerating initial pulse width regulation by the digital memory subsystem 21 to more rapidly achieve optimum performance conditions by quickly bringing the output pulse width over line 17 closer to its ultimate range of preferred operation. In order to accomplish this, th pulse width register is caused to be decremented by a greater number of counts per counting cycle during the start-up phase, to increase the width of the electrical output pulses more rapidly. Typically, instead of increasing pulse width by only 2 counts in the pulse width register each counting cycle, as is done during normal operation, the pulse width is increased by 9 counts during each counting cycle. This increases the width of electrical output pulses much more rapidly than would occur if the optimum pulse width operating range were approached by the much slower 2 count per counting cycle increase in pulse width.

In addition, and only while a start-up phase of operation is in effect, the pulse generation and rate selection subsytem 18 is temporarily set internally by the start-up system 12 to a predetermined output pulse rate most suitable for initial adjustment of pulse width.

The start-up phase continues until a prescribed number of initial drops, typically two drops, have been detected by the drop sensor 11a, at which time the start-up subsystem 12 relinquishes control, and normal output pulse width adjustment, i.e., 2 counts of the pulse width register per counting cycle, occurs for all subsequent drop flow beyond the initial two drops detected.

A duty cycle limitation subsystem 23 overrides the pulse width determination by the digital memory subsystem 21 in the event the pulse width prescribed by the memory subsystem would exceed an appropate maximum duty cycle for the particular output control device 15 being utilized by the system, in order to avoid the possibility of inducing runaway free flow conditions. Such runaway conditions may occur due to mechanical limitations, e.g., inertia, of the output control device 15, and consequent loss of control over fluid flow in the feeding tube may result. The duty cycle of the output control device 15 is defined as the ratio of th time that the output control device is energized, to the total period of time between initiations of successive output pulses over line 17 driving the output control device.

The duty cycle limitation subsystem 23 receives input over line 24 from the pulse generation and rate selection subsystem 18 to enable the duty cycle subsystem to monitor the commanded period between initiation of successive electrical output pulses, as specified by the pulse generation and rate selection subsystem. At the desired duty cycle limitation point for the particular electromechanical output control device 15 being utilized, the duty cycle subsystem 23 terminates the output pulse on line 17 (if it has not otherwise been terminated by the memory subsystem 21), by directing a termination input over line 25 to the output pulse control subsystem 16, thus providing an instantaneous limitation on the electrical output to the mechanical subsystem. Simultaneously, the duty cycle limitation subsystem 23 speeds up the counting rate to the digital memory subsystem 21 so that the counting cycle is completed more rapidly. The latter feature is indicated schematically by an input over line 26 to the memory subsystem 21 from the duty cycle subsystem 23, to alter the counting rate normally provided by a clocking subsystem 27 providing an input over line 28 to the memory subsystem.

The clocking subsystem 27 is also illustrated as driving the pulse generation and rate selection subsystem 18. In this regard, the clocking subsystem 27, while shown for purposes of simplicity as providing inputs only to the pulse generation and rate selection subsystem 18 and digital memory subsystem 21, actually provides clocking inputs to all of the subsystems to maintain synchronous operation wherever required.

The manner in which the duty cycle limitation subsystem 23 increases the counting rate to the digital memory subsystem 21 is by switching, at the duty cycle limitation point, from a counting rate which is normally at one-tenth of the full clock rate, to counting at the full clock rate, whereby completion of the counting cycle is accelerated. The latter featue also insures that the digital memory subsystem 21 will always have completed its last counting cycle prior to initiation of the next counting cycle by a pulse received over line 20 from the pulse generation and rate selection subsystem 18. In the event a high pulse frequency is commanded by the pulse generation and rate selection subsytem 18, the period between initiation of pulses over line 20 may be considerably shorter than the period required for the counting cycle of the digital memory subsystem 21 at the normal counting rate. However, the accelerated counting rate introduced by the duty cycle limitation subsystem 23 insures completion of each counting cycle by the digital memory subsystem 21 even at the highest selected output pulse rates which the overall system is designed to produced.

It has been determined, by experience, that the maximum duty cycle suitable for a typical I.V. controller using an electromagnetically reciprocated I.V. tube pincher, is considerably less than the maximum duty cycle permissible with a stepping motor infusion pump. The reason for this is that the mechanical inertia of th spring-biased I.V. tube pincher is typically of sufficient magnitude that, if the duty cycle is made too large, the pincher cannot close off the feeding tube completely before being required by the next output pulse on line 17 to re-open the feeding tube. This can result in a floating action which fails to completely pinch off the feeding tube and consequently may produce a free flow state. Once such continuous flow occurs, the fluid flow may no longer be divided into incremented drop flow. When no drops are detected by the system, the pulse width will normally be made even wider, making conditions still worse.

It has been empirically determined that, for I.V. controller applications using an electromagnetically reciprocated tube pincher, a duty cycle limitation of 40 percent is preferable, whereas a duty cycle limitation of 75 percent is typically suitable for a positive pressure infusion pump using a d.c. stepping motor drive. Where other types of electromechanical output control devices 15 are utilized, it will be appreciated, of course, that other duty cycle limitations suitable to the particular control device selected, may be prescribed in accordance with the teachings of the present invention.

In the case of the I.V. controller, which is dependent upon gravity induced hydrostatic pressure for inducing drop flow, it is desirable to visually observe an indication of the output pulse width to the control device 15 so that, in the event pulse width is not in the optimum operating range, suitble adjustments can be made in the external I.V. administration system, such as raising or lowering the height of the bottle, to establish proper hydrostatic pressure levels in the feeding tube appropriate to pulse width generation in the desired region of operation. In this connection, a visual pulse width indication subsystem 29 receives information over line 30 from the pulse width register of th digital memory subsystem 21 and decodes the pulse width into pulse width operation ranges.

By means of a pair of lights, the pulse width indication subsystem 29 indicates whether the electrical output pulses being generated by the overall system on line 17 to the output control device 15 fall within defined high, low or optimum pulse width ranges. In a presently preferred embodiment of a visual pulse width indication subsystem suitable for use with an I.V. controller, a green light indicates the low pulse width range, a red light indicates the high pulse width range, while energization of both a red and a green light indicates that operation is in an optimum pulse width range.

An alarms subsystem 14 receives inputs from a timer 31, and from portions of the pulse generation and rate selection subsystem 18, the digital memory subsystem 21, the output pulse control subsystem 16, the memory control subsystem 13, the start-up subsystem 12 and th pulse generator 11b of the drop detection subsystem. These inputs are used, in a manner to be specifically described hereinafter, to monitor system performance so that out-of-limit conditions calling for flow rates in excess of system delivery capability, or indicating a leakage flow rate which cannot be terminated by th output control device, trigger an alarm state which resets the entire system and prevents further system operation until the alarm conditions have been corrected and another start-up phase has been initiated.

The alarms subsystem 14 provides a high level alarm responsive to a demand for an excessive output pulse width over line 17. The subsystem 14 also provides a pair of low level alarms, each one suitable to a different type of output control device 15, and each responsive to specified non-tolerated sequences of pulse width. As will become apparent in connection with the description of the preferred embodiment, the stepping motor infusion pump may operate properly in the negative pulse width region of the pulse width register and, in this regard, the low level alarm provided by the system of the present invention will only be responsive to a requirement for excessive negative pulse width which indicates the possibility of a runaway free flow condition with the pump. However, while the system may continue to operate electrically in the negative pulse region, electrical output to the output control device 15 is gated off during this period of operation and this is indicated schematically by an input over line 33 to the output pulse control subsystem 16 from the alarms subsystem 14.

In addition to the high level and low level alarms, the alarms subsystem 14 is responsive to a lack of detection of any drop flow within a predetermined period of time and as a function of various electrical events occurring in the pulse generation and rate selection subsystem 18, the memory control subsystem 13, the start-up subsystem 12 and the output pulse control subsystem 16. In this connection, the alarms subsystem 14 generates an alarm state if no drops are detected after a prescribed number of pulses has been generated by the pulse generation and rate selection subsystem.

In addition, the system will also alarm in a "no action" mode if, in any prescribed time period during normal operation, there are no drops detected by the drop sensor 11a nor electrical output pulses occurring on line 17. The prescribed time period for the "no action" alarm, is typically approximately 6 minutes, a time interval compatible with the lowest drop rate frequencies which the system might be utilized to generate in normal operation.

Figure 4A:
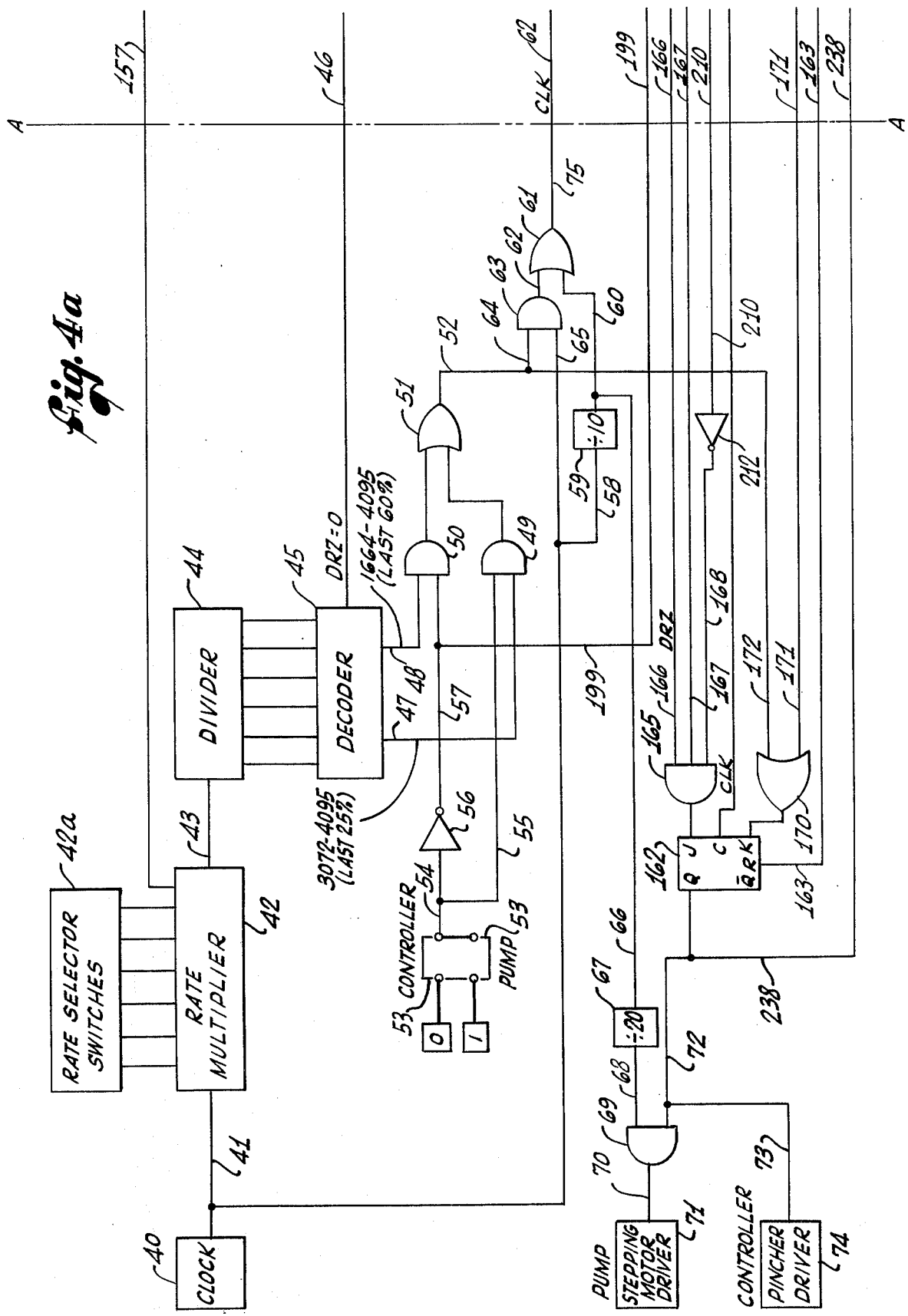
Figure 4C:
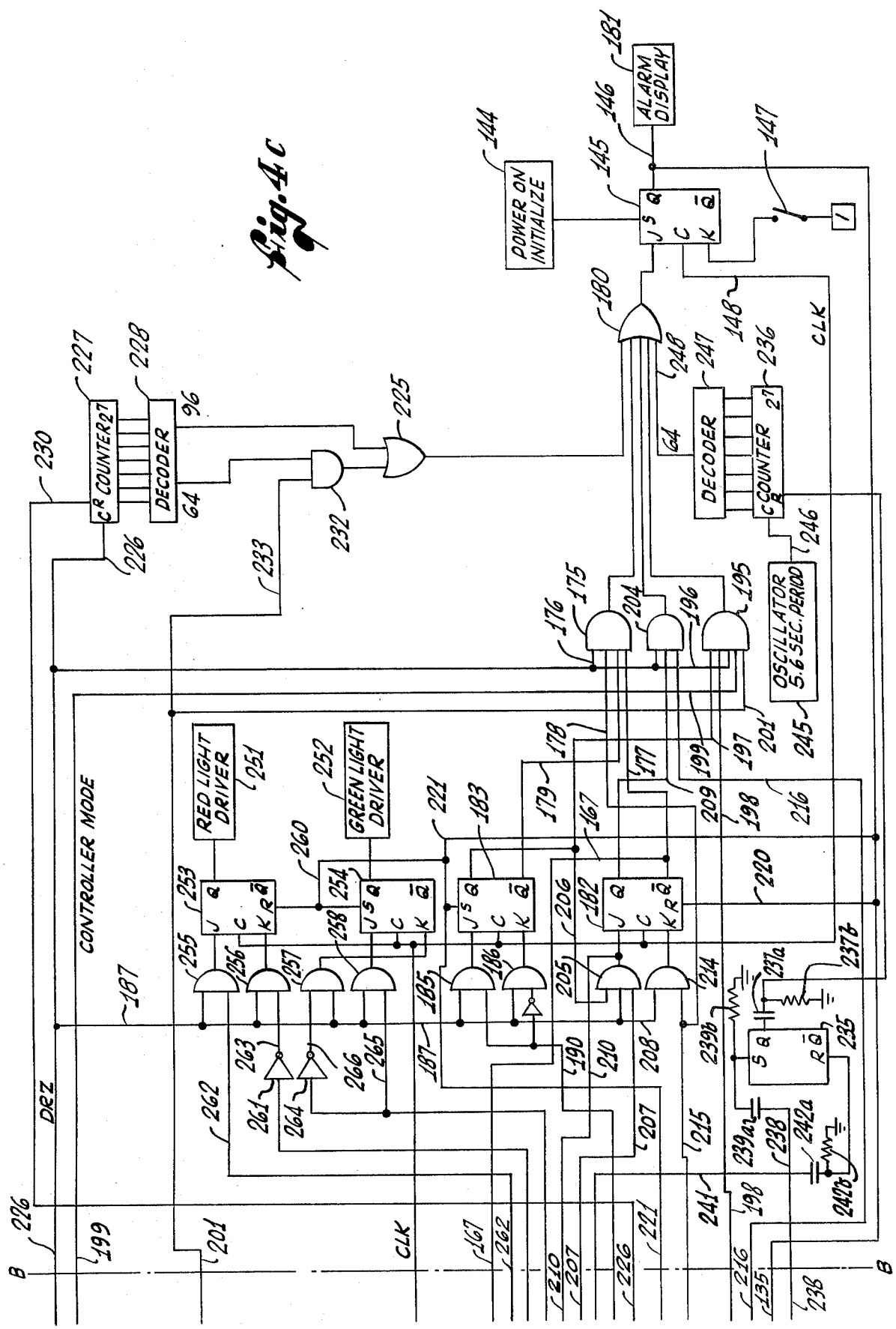

Referring now to FIGS. 4a, 4b and 4c of the drawings, each of these figures are combined block diagrams and electrical schematics of portions of a fluid flow control system in accordance with the present invention, and the figures are arranged with their respective input and output connections aligned so that the three figures can be used as a single drawing for the entire fluid flow control system. In this regard, the various subsystem electrical connections overlap with each other to such a degree that the system is best described with regard to the combined figures, and the balance of the description will accordingly be made with reference to such a composite drawing.

Prior to a detailed description of the operation of the overall system depicted in FIGS. 4a, 4b and 4c, the main elements of each major subsystem area, and their functions, will first be summarized.

FIG. 4a primarily is directed to the input, timing and output sections of the overall system which would include, referring to FIG. 1 previously discussed, the pulse generation and rate selection subsystem 18, the duty cycle limitation subsystem 23, the clocking subsystem 27, the output pulse control subsystem 16 and the output control device 15.

FIG. 4b relates primarily to the memory and control sections of the overall system and, referring again to FIG. 1, primarily includes the digital memory subsystem 21, the drop detection subsystem 11, the memory control subsystem 13 and the start-up subsystem 12.

FIG. 4c is directed primarily to the details of the alarms subsystem 14, the visual pulse width indication subsystem 29 and the timer 31.

Referring now to FIGS. 4a, 4b and 4c as a composite system diagram, a conventional clock generator 40 directs pulses over line 41 to a conventional digital rate multiplier 42 which embodies a plurality of digital rate selector switches 42a.

The rate multiplier 42 multiplies the input frequency by a maximum factor of unity. The output of the rate multipler 42 over line 43 is a pulse rate proportional to the setting of the rate selector switches 42a and, therefore, proportional to the desired drop flow rate to which the system is intended to stabilize. The output of rate multiplier 42 over line 43 is not a continuous pulse train, but rather an irregular burst of pulses, due to the nature of the fractional multiplication which can occur in the rate multiplier. The typically non-uniform pulse train on line 43 is directed to a conventional divider 44 which smooths out the jitter in the pulse train.

The electrical output of the divider 44 is directed to a decoder 45 which decodes out different states of the divider 44 for duty cycle limitation purposes and to generate the reference pulse train for the system which controls the initiation of each counting cycle and the initiation of output pulses from the overall system. The latter is the pulse generated each time the divider 44 is counted to its "zero" state (hereinafter referred to as the "DRZ" signal) and corresponds to the output of the pulse generation and rate selection subsystem 18 of FIG. 1.

The clock frequency generated by the clock 40 is in a presently preferred embodiment of the invention, selected to be 71.68 kilohertz. The rate multiplier 42 multiplies the clock frequency by 1/100th of the drop rate selected and dialed in on the rate selector switches 42a. For example, assuming a selected drop rate of 30 drops per minute, the output frequency on line 43 would be:

input frequency to divider 44 = (71.68 × 30/100) = 21.504 kilohertz

The divider 44 is selected as a register having a count capacity of $2^{12}$ or 4096. Therefore, the output frequency of the DRZ pulse train is:
DRZ frequency = (21.504 × $10^3$/4096) = 5.25 hertz
= 315 pulses/minute It will be noted that the latter result is exactly 10-½ times the selected drop rate of 30 drops per minute. Hence, the clock 40, rate multiplier 42 and divider 44 are selected to provide the desired frequency ratio relationship between the output pulse train and the drop flow rate desired.

The *DRZ* signal output from the decoder 45 is an open loop command signal directed over line 46 to other portions of the system.

Two other output lines 47, 48 from the decoder 45 decode out those states which represent certain counting ranges of the divider 44. The output line 47 from the decoder 45 represents a count of 3072–4095 of the divider 44 which is the last 25 percent of the count capacity of the divider. The line 48 represents a count range of 1664–4095 and represents the last 60 percent of the count capacity of the divider 44.

Therefore, for the time period between successive *DRZ* pulses generated by the decoder 45 over line 46, the decoder output line 48 will be "false" for the first 40 percent of the period and will be "true" for the last 60 percent of the period up to the next *DRZ* pulse. The other output line 47 from the decoder will be "false" for the first 75 percent of the period between *DRZ* pulses and "true" for the last 25 percent. These signals on output lines 47, 48 from the decoder 45, control the duty cycle limitation subsystem. The signals on lines 47 and 48 are fed to a pair of AND gates 49, 50, respectively, which, in turn, direct their outputs to an OR gate 51. The output from gate 51 over line 52 is the duty cycle limitation control signal.

Since the overall system of FIGS. 4a, 4b and 4c, is intended for use with either a pump or a controller, the gates 49 and 50 are used to select the particular duty cycle limitation desired, either a 40 percent or a 75 percent output limitation depending upon the particular output control device intended to be utilized with the system. This is accomplished by a jumper connection 53 which is selectively installed either in the "controller" position or the "pump" position.

Depending upon which operational mode is selected, either an electrical "zone" or an electrical "1" signal is fed over line 54 as input to the duty cycle subsystem. When the "controller" mode of operation is selected, the "zero" input passes over line 55 as a "false" input to the AND gate 49, thus disabling the gate 49. In contrast, the "zero" input is inverted, by an inverter 56, to provide a "true" input over line 57 to the AND gate 50 which will thereby have an output dependent upon the status of line 48 from the decoder 45. Thus, the output of the gate 50, which also passes through the OR gate 51, will be "true" during the last 60 percent of the period between each pair of DRZ pulses.

Similarly, if the "pump" mode is selected, a "1" signal input will be directed over line 54 to the duty cycle limitation subsystem and, hence, gate 49 will be enabled and gate 50 will be disabled, whereby the status of the output line 47 from the decoder 45 will be passed as "true" input to the OR gate 51 whose output over line 52 will be "true" only during the last 25 percent of the period between each pair of *DRZ* pulses.

Hence, it will be apparent that, depending upon which mode of operation is selected, "controller" or "pump", a duty cycle limitation of either 40 percent or 75 percent, respectively, will be imposed on the system as represented by the signal on line 52.

The output of the clock generator 40 is also directed over line 58 to a divide by the counter 59 which divides the clock frequency by a factor of 10 and feeds the reduced clock frequency over line 60 to an OR gate 61. The OR gate 61 also receives an input over line 62 from an AND gate 63 which has as its inputs the duty cycle control signal on line 64 and the full rate clock signal on line 65. Hence, the output of the OR gate 61 over line 75 is the clocking signal (hereinafter referred to as the "CLK" signal) for the entire system.

The CLK signal will, however, change its frequency from the full clock rate produced by the clock generator 40 to one-tenth of the maximum clock rate depending upon whether or not the duty cycle limitation signal is "true". Therefore, depending upon whether the "controller" or "pump" mode has been selected, the CLK signal will start out, after a *DRZ* pulse, at one-tenth of the maximum clock rate and, when the duty cycle control signal on line 52 is "true", the CLK signal will increase its frequency to the full clock rate for either the last 60 percent (controller mode) or the last 25 percent (pump mode) of the period prior to the next *DRZ* pulse. As will subsequently be apparent, since the CLK signal counts up the memory subsystem, the portion of a counting cycle which follows after a "true" duty cycle limitation signal on line 52 is counted up at an accelerated rate.

The output of the divider 59 is also fed over line 66 to another divider 67 which divides the pulse frequency by two to provide an output frequency over line 68 which is the pulse drive source used to run the stepping motor of a pump. In this regard, the pulse train over line 68 is passed through an AND gate 69 over line 70 to the stepping motor driver 71 only when an enabling input over line 72 from the output pulse control subsystem is also directed to the gate 69. The particular dividers 59 and 67 conveniently provide a driver pulse source for the stepping motor driver 71 at a selected stepping frequency of 360 hertz. This stepping motor frequency is computed by dividing the clock frequency of 71.68 kilohertz by 10 and then by 20 to obtain a pulse frequency of approximately 360 hertz. This arrangement avoids the necessity of providing a separate driver pulse source for the stepping motor driver.

The output control pulse provided on line 72 as input to the gate 69 is also directed over line 73 to a pincher dirver 74 when the system is being used in the "controller" mode of operation. In the case of the controller, the output control pulse is actually the energizing pulse itself for the output control device, whereas in the case of a stepping motor pump, the output pulse simply controls the duration or gating of a burst of pulses from the stepping motor driver pulse source.

Referring now more particularly to FIG. 4b, the digital memory subsystem includes a pair of counters, the scanning control register 83 and the pulse width register 85. A decoder 84 is associated with the scanning control register 83, while a decoder 86 is associated with the pulse width register 85. The scanning control register 83 is controlled by an input AND gate 87 and the pulse width register 85 is controlled by an input AND gate 88. The gates 87, 88 gate the counting signal CLK into their respective registers at the appropriate times. As will be recalled from the previous description of the duty cycle subsystem, the CLK signal may be either the full rate clock signal of 71.68 kilohertz or it ca be only one-tenth of that frequency, i.e., 7.168 kilohertz. The higher rate clock signal is in effect whenever the duty cycle limitation is imposed.

Each of the registers 83 and 85 has a count capacity of $2^{10}$ or 1024. Basically, what occurs in the digital memory and control subsystems is that the scanning control register 83 and the pulse width register 85 undergo a counting cycle which is initiated each time a *DRZ* pulse is generated at the output of the decoder 45 on line 46, and each counting cycle must be completed before the next DRZ pulse is produced.

The control register 83 determines the duration of each counting cycle for itself and the pulse width register 85, by initiating the counting cycle from its "zero" state upon receipt of a DRZ pulse, and terminating the counting cycle when it counts to 1024 (the return to its "zero" state). The control register 83 then remains in its "zero" state until the next DRZ pulse is produced at the output of the decoder 45.

Normally, the pulse width register 85 is caused to lag the control register 83 by two counts during each counting cycle, thereby increasing the pulse width of the output pulses controlled by the register 85, as measured by the difference between the count in the register 85 and its "1024" ("zero") overflow state.

Each time a drop is detected, the pulse width register 85 is incremented by 21 counts relative to the control register 83 to narrow the effective output pulse width as measured by the count in the register 85. This establishes the desired (21/2 or 10-½ ratio desired for the output pulse frequency to the drop flow rate frequency. In essence, the pulse width is servoed in a closed digital loop to preserve the desired 10-½ ratio which is forced on the system by the DRZ pulse rate produced by the pulse generation and rate selection subsystem.

The decrementing of the register 85 relative to the control register 83 is accomplished in each counting cycle by holding off CLK pulses from the register 85 for the first 2 counts received by the control register 83 during each counting cycle. The incrementing of the pulse width register 85 relative to the control register 83, each time a drop is detected, is accomplished by holding off CLK pulses from the control register 83 when the pulse width register 85 reaches its "zero" state after drop detection, and resuming counting of the control register 83 only after the pulse width register has reached a count of "21". Hence, pulse width is effectively increased and decreased by altering the relative counting states or phase existing between the scanning control register 83 and the pulse width register 85 in the digital memory subsystem.

As previously indicated, during the start-up phase of operation, defined as the time to receive the first two drops after initially turning on the system or coming out of an alarm state, the control relationship between the control register 83 and the pulse width register 85 is altered so that pulse width is increased by 9 counts during each counting cycle, rather than by only two counts, to more rapidly bring the system up to its normal pulse width operating region.

The size, i.e., count capacity, of the registers 83 and 85, and the number of counts by which pulse width is increased and decreased, is determined in accordance with the desired resolution of the overall system and the loop gain desired. It has been determined empirically, for the type of output control devices utilized and the degree of stability desired that, for a system capable of generating (in the "pump" mode) a drop rate of 99 drops per minute, a full range count capacity of 50 drops for the registers, with a loop gain of approximately 2 percent is desirable.

For a full range of 50 drops, at an increment of 21 counts for each drop detected, a register count capacity of 1024 appears to be optimum. This is also desirable since the maximum increment of 21 counts per drop detected is approximately 2 percent of the count capacity, which satisfies the loop gain requirements. Too high a loop gain, i.e., the percent of change generated in the system for each drop detected, would cause the system to react too rapidly with possible overshoot and oscillation. A lower loop gain approaches proportional servo control more closely and is much more reliable than the large on-off type swings in the system which tend to occur with excessively high loop gain.

The count capacity of 1024 for the registers 83 and 85 is also compatible with the maximum pulse width requirements for the system. In this regard, the output control mechanism utilized may require a maximum pulse width of approximately 140 milliseconds and, therefore, the registers 83 and 85 must be capable of a complete counting cycle from "zero" to "1024" of at least 140 millisecond at the counting rate of the CLK signal. In this regard, using the normal (no duty cycle limitation imposed) CLK frequency of 7.168 kilohertz, the maximum pulse width $P_M$ capable of generation with the count capacity of 1024 is:

$$P_M = (1024/7.168) \times 10^3 = 0.1428 \text{ seconds} = 142.8 \text{ milliseconds}$$

Such a maximum pulse width is normally required only at very low drop flow rates.

In addition, it will be noted that, at the highest selectable drop rate of 99 drops per minute typically intended for the system of the present invention, the time between DRZ pulses is considerably shorter than the maximum counting cycle period of 143 milliseconds. In this connection, at a selected drop rate of 99 drops per minute, the period $P_P$ between DRZ pulses is:

$$P_P = (60 \text{ seconds}/99 \text{ drops/min.}) \times 10.5 = 0.058 \text{ seconds} = 58 \text{ milliseconds}$$

However, it can be shown that, at such high drop rates, the duty cycle limitation subsystem will (at 40 percent of the period between DRZ pulses for the controller mode and at 75 percent of the period between DRZ pulses for the pump mode) switch the CLK signal from 7.168 kilohertz to the maximum clock rate of 71.68 kilohertz. This enables the counting cycle to be completed at a very fast rate, terminating the output pulse prematurely and thereby limiting it to the designated duty cycle. Inevitably, this also shortens the counting cycle sufficiently to assure completion of the counting cycle prior to appearance of the next DRZ pulse.

The aforementioned operation of the digital memory subsystem and the duty cycle limitation subsystem is illustrated in FIGS. 5a through 5h of the drawings. FIG. 5a represents the regular occurrence of DRZ pulses which initiate each counting cycle of the memory subsystem. FIG. 5b represents the variation of CLK frequency during the period between successive DRZ pulses and shows the change in frequency from 7.168 kilohertz to a full clock rate ten times greater, or 71.68 kilohertz, after the duty cycle period of 40 percent has been reached.

FIGS. 5c, 5d and 5e illustrte the states of the control register 83 and pulse width register 85 and the nature of the output pulse on line 72, where normal operation is such that the duty cycle has no effect upon the output pulse width as where narrow output pulses are called for. In contrast, FIGS. 5f, 5g and 5h illustrate the various states of the control register 83 and pulse width register 85 and the nature of the output pulses on line 72 where the duty cycle does impose a limitation upon output pulse width.

Referring to FIGS. 5c and 5d, the control register 83 starts the counting cycle from its "zero" state, with the pulse width register 85 at an initial starting state of "924" which is a relatively narrow pulse width. The pulse width register 85 counts up to its "zero" state prior to the duty cycle limitation being imposed and then continues to be counted up until it reaches its final state of "922" (2 counts less than its original starting state) which occurs at the same point that the control register 83 passes through its "zero" state. It will also be noted that the memory counting cycles are completed considerably more rapidly due to the higher frequency of the CLK signal after imposition of the duty cycle limitation than would have been required if the duty cycle limitation had not been imposed, as indicated by the fictitious counting states denoted in parenthes in FIGS. 5c and 5d.

The output pulse width on line 72, as illustrated in FIG. 5e, is determined by the pulse width register 85 in counting from the "924" state to the "zero" state, and defines a relatively narrow pulse width well within the duty cycle limitation.

Referring now to FIGS. 5f, 5g and 5h, the control register 83 starts out again in its "zero" state, the second "zero" position representing the speeded up completion of the counting cycle, with the third "zero" position indicating the starting point for the next counting cycle as triggered by the next DRZ pulse. The "zero" position shown in parentheses corresponds to the same position in FIG. 5c which indicates how long it would have taken to complete the counting cycle if there had been no switching to a higher CLK frequency because of the duty cycle limitation.

FIG. 5g shows the pulse width register 85 starting out with a relatively low count of 124 which would normally produce, in the absence of the duty cycle limitation, a very wide output pulse on line 72. The first "122" state shown for the pulse register 85 represents its state at the end of the counting cycle completed on an accelerated basis. The pulse register 85 remains in the "122" state until the next DRZ pulse. The states indicated in parentheses indicate where the pulse register would have been had there been sufficient time for the register to count up without a duty cycle limitation. In this regard, the figures shown in parentheses on FIGS. 5c, 5d, 5f and 5g are situations which assume that the DRZ pulse frequency was sufficiently low, substantially lower than that illustrated in FIG. 5a, that the counting cycle could be completed prior to any duty cycle limitation being imposed, i.e., there was adequate time left for the counting cycle to be completed at the normal CLK frequency of one tenth of the maximum clock rate.

FIG. 5h illustrates that the output pulse on line 72 is terminated by imposing the duty cycle limitation, even though the electronics of the memory subsystem continue to count up both the control register 83 and the pulse width register 85. In this regard, note that the output pulse is terminated by the duty cycle limitation rather than the "zero" state of the pulse width register 85. The dotted curve in FIG. 5h illustrates what the pulse width of the output pulse on line 72 would have been if no duty cycle limitation had been imposed.

With the aforedecribed background in mind, the following more detailed description of the digital logic employed in the overall system will be more readily understood.

When the scanning control register 83 reaches a count of "1024" during a counting cycle, i.e., its "zero" state, the zero output line from the decoder 84 provides a "true" output on line 90 which is inverted by an inverter 91 to disable an AND gate 92. Hence, the output of the AND gate 92 on line 93 is "false" which produces a "false" output from the OR gate 94 over line 95 to disable the input AND gate 87 to the control register 83. This prevents the CLK signal from counting up the control register 83 any further and effectively terminates the counting cycle at the "zero" state of the control register.

The other input to the OR gate 94, over line 96, is the DRZ signal which passes through the gate 94 and enables AND gate 87 to again pass the CLK signals to the control register 83, thereby initiating a new counting cycle. Hence, the DRZ signal overrides the inhibiting effect of the "zero" state of the control register 83 at the beginning of each new counting cycle.

After the first counting pulse (DRZ and CLK) is received by the control register 83, the "zero" output line 90 from the decoder 84 goes "false" which, in turn, makes the output of the inverter 91 to go "true" and thereby enables gate 92. The other input to the AND gate 92, over line 97, is also normally "true", so that the output line of gate 92, over line 93, passes through OR gate 94 to maintain the AND gate 87 enabled for further passage of the CLK pulses to the control register 83 even though the DRZ pulse is no longer available. Hence, the DRZ pulse merely initiates the counting cycle which then continues until completion.

The input AND gate 88 to the pulse width register 85 is likewise disabled by the "zero" state of the control register 83 since it receives the same inverted output as the gate 92. Thus, the pulse width register 85 does not yet begin to count when the DRZ pulse causes the control register 83 to count from the "zero" state to the "1" state.

Another input to the AND gate 88 of the pulse width register, over line 99, is the $\overline{Q}$ output of a flip-flop 98. Hence, the flip-flop 98 must be "false" ($\overline{Q}$ would then be "true") for the AND gate 88 to be enabled after the counting cycle has been initiated. In this regard, the J input of the flip-flop 98 is set by the same DRZ pulse that enables the control register 83 to be counted from zero to "1". Therefore, on the very next CLR pulse, which counts the control register 83 from "zero" to "1", the flip-flop 98 is set "true" which, of course, makes the $\overline{Q}$ output over line 99 to gate 88 "false". However, the input gate 88 to the pulse width register 85 remains disabled, even though the input to the gate 88 over line 100 from the inverter 91 is now "true". Hence, the control register 83 has been counted to its "2" state, with no counts having yet been passed to the pulse width register 85 during the counting cycle.

From the foregoing analysis, it will be apparent that the pulse width register 85 will not count until the flip-flop 98 is reset so that its $\overline{Q}$ output is "true". This requires that the K input of the flip-flop 98 be set. The K input of flip-flop 98 is under the control of three gates, an OR gate 102 and a pair of AND gates 105, 106 whose outputs are directed over lines 107, 108, respectively, as inputs to the OR gate 102.

The AND gate 106 receives as input, over line 109, the "1" state of the control register 83 decoded out by the decoder 84, and receives as a second input, over line 110, the $\overline{Q}$ output of a flip-flop 114 which is the start-up control flip-flop indicating whether or not the system is in the start-up phase of operation. The other AND gate 105 receives as one input, over the line 111, the "8" state of the control register 83 from the decoder 84, and receives as a second input, over line 112, the Q output from the start-up flip-flop 114.

When the system is in the start-up phase of operation, the flip-flop 114 will be "true" (its Q output will be "true") whereas, when the system is out of the start-up phase, as will typically be the case for the bulk of normal operation, the flip-flop 114 will be false (its $\overline{Q}$ output will be "true").

Assuming for purposes of the present analysis that the system is out of the start-up phase, then the $\overline{Q}$ output of the start-up flip-flop 114 will be "true". Therefore, when the control register 83 has been counted to its "" state, the AND gate 106 will be enabled, and its "true" output will be passed by the OR gate 102 to set the K input of the flip-flop 98. On the very next CLK pulse, the control register 83 will be counted from its "1" state to its "2" state, the pulse width register 85 will remain unchanged, and the flip-flop 98 will be reset so that its $\overline{Q}$ output will be "true" prior to receipt of the next CLK pulse.

At this point, both of the inputs over lines 99 and 100 to the pulse width register input gate 88 are "true", so that the very next CLK pulse is passed both to the control register 83 and the pulse width register 85. Hence, the pulse width register 85 receives its first count as the control register 83 is counted to its "3" state, thereby resulting in the pulse width register having been decremented by a count of two relative to the count in the control register. The gates 87 and 88 continue to be enabled for the passage of additional CLK counting pulse for the balance of the counting cycle, in the absence of drop detection, until the control register 83 again counts to its "zero" state, at which time both of the gates 87 and 88 are disabled by the "zero" state output from the decoder 84 which is inverted by the inverter 91 in the manner previously described. Hence, during each counting cycle, the pulse width register is decremented by two counts to produce an increase in pulse width for the output pulses generated by the system.

As previously indicated, when a drop occurs, it is desired to increment the pulse width register by 21 counts relative to the control register 83 in order to narrow the output pulse width from the system. The pulse width then increases in steps of two counts each, as previously described in connection with FIG. 3 of the drawings.

The addition of 21 pulses to the pulse width register 85 during a counting cycle will, of course, also include a decrement of two pulses during that same counting cycle, in the manner previously set forth, thus resulting in a net increase during the counting cycle following drop detection of 19 pulses incremented into the pulse width register 85 relative to the control register 83.

When a drop occurs, it is detected by a drop detector 115 of the drop detection subsystem, to produce a pulse over line 122 to the "S" or "set" input of a drop detection flip-flop 118. The drop detection pulse immediately sets the flip-flop 118 non-synchronously (independent of the receipt of a CLK pulse) in conventional set-reset flip-flop manner. Hence, upon drop detection, the flip-flop 118 is immediately forced into its "true" state which makes its Q output on line 123 go "true" as one input to an AND gate 120. The other input to the AND gate 120, over line 124, is the high order flip-flop of the pulse width register 85, indicated as the 512-1023 output line from the decoder 86 of the pulse width register.

Assuming for the moment that the pulse width register 85 is in its high count state, which provides a "true", output over line 124, the output of the AND gate 120 will be "true" and will set the J input of a flip-flop 119. On the very next CLK pulse, the flip-flop 119 will be "set" so that its Q output will go "true". The "true" state of the flip-flop 119 is fed over line 125 to the K input of the drop detection flip-flop 118 so that, the next CLK pulse, the drop detection flip-flop is "reset" and the gate 120 is thus disabled.

Hence, the flip-flop 119 is always set "true" after the flip-flop 118 has been set "true" and the pulse width register 85 has counted up to the state where its high order flip-flop is "true". When the Q output of the flip-flop 119 is "true", its $\overline{Q}$ output over line 127 is "false" which disables one of the inputs to an OR gate 121. The other input to the OR gate 121 is the high order state of the pulse width register 85, over line 125, from the decoder 86. When the latter line is "true", the output of the OR gate 121 is "true" and its input over line 97 to the AND gate 92, previously discussed, continues to enable gate 92 and permit the control register 83 to be counted at times other than when the control register is in its "zero" state.

On the other hand, when the flip-flop 119 is "true" and the pulse width register 83 is not in its high order counting state, e.g., when the pulse width register has just gone from its "1023" state to its "zero" state, the output on line 124 will be "false" and the $\overline{Q}$ output on line 127 will also be "false", resulting in the gate 92 being disabled so that further counting of the control register 83 is arrested. Hence, after a drop has been detected, the control register 83 is gated off when the pulse width register 85 counts "zero".

Once the control register 83 is thus gated off, further counting of the control register will not resume again until either the pulse width register 85 counts to its high order range 512-1023 or the flip-flop 119 is set "false" so that its $\overline{Q}$ output over line 127 is "true". It will be observed that the K input of the flip-flop 119 is set by the "20" output from the pulse width register decoder 86 over line 129. Hence, when the pulse width register 85 has counted to "20", the K input of the flip-flop 119 is "set" and, on the next CLK pulse, the pulse width register counts to its "21" state while the flip-flop 119 is "reset" to make its $\overline{Q}$ output "true" over line 127. Therefore, on the next CLK pulse which counts the pulse width register 85 to its "22" state, the control register 83, again enabled by a "true" output from the OR gate 121, also receives the CLK pulse and is counted. This results in a suppression of 21 counts in the control register 83 relative to the pulse width register 85, which is equivalent to incrementing the pulse width register relative to the control register by 21 counts. At this point, both registers 83 and 85 continue to run until the control register 83 again goes to "zero", at which time both registers stop. Upon receipt of the next DRZ pulse, the control register 83 will again start counting, followed by the pulse width register 85 two counts later in the manner previously described.

Having thus described the manner in which the scanning control register 83 and the pulse width register 85 are incremented and decremented relative to each other, and the effects of counting cycle initiation by the DRZ pulse and of drop detection, several typical situations will next be illustrated. In this regard, illustrative cases will be considered where a drop has been detected between counting cycles, i.e., after both registers 83 and 85 have come to rest and are awaiting a DRZ pulse to initiate the next counting cycle. This category of investigation will be extended to those situations involving a variety of different starting states for the pulse width register 85. In addition, cases will be considered for various relative states of the control register 83 and pulse width register 85, where a drop is detected while a counting cycle is actually in process. FIGS. 6a–6c cover those situations where a drop is detected between counting cycles, whereas FIGS. 6d–6g cover those situations where a drop is detected during a counting cycle.

FIG. 6a is a table of the relative states of the control register 83 and the pulse register 85, and also shows the states of the flip-flops 118 and 119, where the registers came to rest at "zero" in the control register and a count of "18" on the pulse width register 85 in the preceding cycle. A drop was then detected which set the flip-flip 118 "true" immediately. Ultimately, a DRZ pulse occured which initiated the counting cycle. The states shown in the first line of the table are, therefore, the starting states at the beginning of the next counting cycle after the drop occurred.

The pulse width register 85 is inhibited by two pulses as the control register 83 is counted, so that the register 85 is counted from "18" to "19" only as the control register is counted from "2" to "3". The flip-flop 119 which is normally "false" remains "false", because of the "false" output on line 124 from the high order 512–1023 output of the pulse width register decoder 86 which disables the gate 120 input to the flip-flop 119.

Both flip-flops 118 and 119 remain unchanged as the registers 83 and 85 are counted up, until the pulse width register 83 is counted to "512". At the latter count of the pulse width register 85, line 124 goes "true", enabling the gate 120 and setting the J input of the flip-flop 119, so that on the very next CLK pulse, which counts the pulse width register 85 to "513", the flip-flop 119 is set "true". This disables the $\overline{Q}$ output of the flip-flop 119 over line 127, which is replaced by the "true" output on line 124 from the decoder 86, so that the control register 83 can continue counting. On the next CLK pulse, which counts the pulse width register 85 to its "514" state, the drop detection flip-flop 118 is "reset", its K input having been previously "set" by the Q output on line 125 from the flip-flop 119.

Both registers 83 and 85 are then counted continuously until the pulse width is in its "zero" state, at which time the 512–1023 output line 124 from the decoder 86 goes "false". Since the $\overline{Q}$ output from the flip-flop 119 over line 127 is also "false" (the flip-flop 119 having previously been set "true"), both inputs to the OR gate 121 are "false" and the control register 83 is thus gated off at its count of "1008".

When the pulse width register 85 is counted to its "20" state, the K input of the flip-flop 119 is "set" and, when the register 85 is counted to "21", the CLK pulse also resets the flip-flop 119 so that the $\overline{Q}$ output on line 127 is "true". This again enables the control register 83, so that the CLK pulse which increments the pulse width register 85 to its "22" state is also passed to the control register 83 to count the latter register to "1009". Both registers continue to count, with both flip-flops 118 and 119 "false", until the control register 83 counts to "zero", at which time the counting cycle terminates with a count of "37" in the pulse width register 85. Since the pulse width register 85 started out with a count of "18", this represents a relative increment of 19 counts, which include both the 21 count increment due to drop detection and the normal two count decrement experienced during each counting cycle.

FIG, 6b illustrates the situation where the state of the pulse width register 85 was "512" upon completion of the previous counting cycle and at the beginning of the counting cycle illustrated. Under those circumstances, since the flip-flop 118 was set "true" immediately upon detection of the drop, and the 512–1023 output line from the decoder 86 provides a "true" output over line 124 to the AND gate 120, the very next CLK pulse sets the flip-flop 119 "true" and the next CLK pulse after that resets the flip-flop 118, all prior to the DRZ pulse which inititiates the next counting cycle. Hence, the counting cycle starts out with the control register 83 in the "zero" state, the pulse width register 85 in the "512" state, the flip-flop 119 "true" and the flip-flop 118 "false".

When the pulse width register 85 is ultimately counted to "zero", the output of the OR gate 121 again goes "false" to gate off the control register 83 (as in the case illustrated in FIG. 6a) until the pulse width register counts to "20". In going from count "20" to count "21" in the pulse width register 85, the flip-flop 119 is "reset", making its $\overline{Q}$ output go "true" one line 127, thus enabling the control register 83. Both counters are continuously counted for the remainder of the counting cycle as pulse width register 85 is counted by the next CLK pulse to its "22" state and the control register is counted to state "515". Counting of both registers proceeds until the control register 83 is counted to "zero", at which time the count in the pulse width register 85 is "531", again 19 counts more than the starting count of 512.

FIG. 6c illustrates the case where the state of the pulse width register at the termination of the last counting cycle and at the beginning of the present counting cycle is "1023". For the same reasons as in the case illustrated in FIG. 6b, flip-flop 119 has been set "true" and flip-flop 118 has been reset to its "false" state. The pulse width register 85 is again inhibited for two counts and then, as the control register 83 counts to its "3" state, the pulse width register overflows to "zero" which gates off the control register for 21 counts.

As the pulse width register 85 is counted to "22", the control register 83, having been again enabled in the manner previously described for these conditions, is counted to its "4" state. Counting again continues until the control register 83 is counted to "zero", thus terminating the counting cycle.

It will be noted in FIG. 6c that the pulse width register 85 passes through its "zero" state a second time during the counting cycle, but without gating off the control register 83, since the flip-flop 119 is "false" during this second overflow of the pulse width register and, therefore, a $\overline{Q}$ "true" output over line 127 to the OR gate 121 continues to enable the control register 83. At the conclusion of the counting cycle, the count in the pulse width register 85 is "18" which, again, is 19 counts more than its starting state of "1023".

FIG. 6d illustrates the situation where a drop occurs during a counting cycle when the control register 83 is in its "1" state and the pulse width register 85 is at count "18". The flip-flop 118 is set to its "true" state immediately upon drop detection, but since the 512–1023 output line from the decoder 86 of the pulse width register is "false", the flip-flop 119 must remain "false" until the pulse width register is counted up to 512. It will be apparent, upon comparison, that the situation of FIG. 6d essentially duplicates that previously described in connection with FIG. 6a.

FIG. 6e illustrates the case where a drop is detected when the control register is in the "1" state and the pulse width register 85 is already in its high order decade of operation at a count of "512". Under these circumstances, flip-flop 118 is set "true" immediately on detection of the drop and the latter state over line 123 is immediately passed by the AND gate 120 to set the J input of the flip-flop 119. On the next CLK pulse which counts the control register 83 from "1" to "2", the flip-flop 119 is set "true". On the next CLK pulse after that, the drop detection flip-flop 118 is reset. Again, the control register 83 has been counted up while the pulse width register 85 has been inhibited for two counts. At this point, the counting cycle proceeds exactly as for the case illustrated and described in connection with FIG. 6b.

FIG. 6f illustrates the case where a drop is detected at that point in the counting cycle when the control register 83 is at a much higher count of "500" and the pulse width register is at a count of "15". Again, the flip-flop 38 is immediately set "true" while the flip-flop 119 remains "false" until the pulse width register counts up to 512, at which time the flip-flop 39 is set "true" as the pulse width register is counted to "513". On the very next CLK pulse, the "true" output of the flip-flop 39 resets the flip-flop 118 to its "false" state.

At this point, both registers are counted up until the control register reaches "zero", at which time both registers stop and must wait until the next DRZ pulse to start another counting cycle. It will be apparent, from the counting states depicted in FIG. 6f, that, for the conditions stated, the incrementing of the pulse width register in response to drop detection is not accomplished in the same counting cycle in which the drop is actually detected, but is delayed until the next counting cycle. In this regard, the next DRZ pulse initiates the next counting cycle, which then inhibits the pulse width register 85 by two counts and increments the pulse width register by 21 counts in the same manner as previously described in connection with the case illustrated in FIG. 6b. Note in FIG. 6f that the pulse width register 85 comes to rest at a count of "558" which is 19 counts more than the "539" state at the beginning of the counting cycle.

FIG. 6g illustrates the case where a drop is received with a relatively high count of "600" in the control register 83 and with a relatively low count of "15" in the pulse width register 85. The primarily distinction between FIG. 6g and FIG. 6f previously described, is that the control register 83 overflows to its "zero" state prior to the pulse width register 85 arriving at its high order count of 512.

In FIG. 6g, the counting cycle in which the drop was actually detected is again completed without any incrementing of the pulse width register 85. As in the case of FIG. 6f, the 21 count increment is deferred until the next counting cycle.

The next counting cycle begins with a DRZ pulse, the control register 83 in the "zero" state and the pulse width register at "439". The flip-flop 118 has been set "true" by the drop detection, but the flip-flop 119 remains "false" until the pulse width register 83 counts up to "512". The pulse width register 83 is again inhibited by two counts as the control register 83 is counted up and, when the pulse width register overflows to its "zero" state, the control register is inhibited for 21 counts, all essentially as indicated for the case previously described in connection with FIG. 6a. In this regard, note that the final count in the pulse width register 85 is "458" whereas its initial count state at the beginning of the last complete counting cycle was "439", representing the desired net increment of 19 counts.

Normally, in the "controller" mode, drops come at regular periodic intervals. However, in the "pump" mode of operation, it is possible to receive a burst of drops in view of the larger body of liquid trapped between the cam followers of the pump. In the event a second drop occurs before a previous drop has been completely accounted for, it can be shown that the second drop is ignored by the system. For example, if the flip-flop 118 has been set "true" and the flip-flop 119 is still "false", the second drop has absolutely no effect on the drop detection flip-flop 118 since the latter flip-flop is already "set". In the situation where the drop detection flip-flop is "false" and the flip-flop 119 is already "true", the drop detection flip-flop 118 will immediately be "set" again by the second drop but will also be "reset" to its "false" state again on the next CLK pulse, because of the "true" state of the flip-flop 119 communicated to the K input of the drop detection flip-flop.

For certain types of electromechanical output control devices, particularly those capable of responding properly to very narrow pulse width input, the system of the present invention is capable of functioning normally on an expanded low level operational basis, without going into alarm, by storing and processing the equivalent of negative pulse width in the pulse width register 85. In the embodiment of the invention illustrated, this type of operation is possible with the system operating in the "pump" mode.

The negative pulse width condition may occur with normal low level operation in which extremely narrow pulse widths are generated, so that further incrementing of the pulse width register 85 upon detection of drops causes the pulse width register to overflow and start counting up again. Overflow of the pulse width register is countwise is equivalent to underflow of pulse width, i.e., negative pulse width, which is manifested by the sudden transition from a very narrow output pulse (a high count in the pulse width register) to a very wide output pulse (a very low count in the pulse width register).

Assuming the system is operating to provide normal fluid flow, i.e., there are no flow conditions warranting generation of an alarm state, the negative pulse width condition in the pulse width register 85 will be only transitory and successive decrementing by two counts per counting cycle will cause the pulse width register to underflow and come out of the negative pulse width region, to thereby restore normal narrow output pulse generation manifested by a high count state in the pulse width register.

During operation of the system with apparent negative pulse width, the alarms subsystem generates an output (without going into an alarm state), in a manner to be subsequently described, to gate off the system output pulses which would otherwise normally appear on line 72 (FIG. 4a) while allowing the memory subsystem to continue to function normally. This capability of operation in the negative pulse width region of the pulse width register enables an expanded dynamic range of operation without the need for expanding the count capacity of the registers in the digital memory.

FIGS. 7 and 8 of the drawings are next described to further clarify system operation under negative pulse width conditions.

FIG. 7a illustrates a typical output pulse on line 70 to the stepping motor driver 71. FIG. 7b shows the corresponding drive pulses which are passed to energize the steppping motor of the pump and it will be observed that the response of the motor to the output pulse of FIG. 7a is essentially very nearly instantaneous, with very little apparent mechanical inertia.

FIG. 8a shows a rather narrow memory pulse, which is the solid curve in this figure, while FIG. 8b shows a single motor drive pulse generated within the memory pulse period, again indicating essentially no delay in response of the motor.

FIG. 8a also shows a dotted curve which indicates a further reduction in pulse width by an incrementing of 21 counts and decrementing of two counts in the pulse width memory 85 during the next counting cycle after a drop has occurred. Since the initial pulse width in FIG. 8a is assumed to be extremely narrow, the net increment of 19 counts in the next counting cycle will yield a negative pulse width which is shown in FIG. 8c as an extremely wide memory pulse due to overflow of the pulse width register 85.

FIG. 8d illustrates that there is no motor pulse output since, in a manner which will be subsequently hereinafter decribed, the output pulse on line 70 is gated off whenever the pulse width register is operating in the negative region.

FIG. 9a illustrates an output pulse on line 73 for the controller case. FIG. 9b indicates the corresponding controller mechanism response and illustrates the typical effects of mechanical inertia encountered with such devices.

FIG. 10a illustrates a very narrow memory pulse produced while operating in the "controller" mode. FIG. 10b illustrates that, even though the system is not operating in the negative pulse width region, there is no mechanical output from the controller because of the mechanical inertia which introduces a delay greater than the memory pulse width.

The next portion of the description is directed to the start-up phase of operation of the overall system. As previously indicated, the major difference in the start-up mode of operation is that, instead of altering the pulse width in the pulse width register 83 by only two counts in each counting cycle, the pulse width register is decremented by nine counts in each counting cycle until the first two drops have been received. Then the system switches back to normal operation by continuing to decrement the pulse width register 83 two counts per counting cycle. In addition, and only while a start-up phase is in process, the output pulse rate is temporarily set internally to a prescribed rate most suitable for initial adjustment.

When the system first starts out, either during "power on" initialization, or during alarm, all of the flip-flops and registers are forced into certain specified states. In this regard, both of the registers 83 and 85 are reset to "zero" over lines 133 and 135, respectively. The flip-flops 118 and 119 are "reset" over line 136, flip-flop 98 is "reset" over line 137, and the start-up flip-flop 114 is set to its "true" state on line 138. In addition, a flip-flop 140, which is part of the start-up subsystem, is "reset" over line 141. The purpose of the flip-flop 140 is to keep track of receipt of the first drop in the start-up phase of operation.

Referring briefly to FIG. 4c, when the system is first turned on, a power-on initializing circuit 144 sets the input of an alarm flip-flop 145 immediately so that the Q output of the flip-flop 145 is "true" on line 146 and all of the system flip-flops and registers can be set and reset appropriately for start-up conditions. A start-up switch 147 is then closed which "sets" the K input of the flip-flop 145 so that on the next CLK pulse over line 148, the flip-flop 145 will go "false".

The first DRZ pulse will start the control register 83 counting in the normal fashion, with the initial counts being inhibited from the pulse width register 85. However, since the start-up flip-flop 114 has been set "true", gate 106 is disabled and gate 105 is now enabled. As a result, the "8" state of the control register 83, rather than the "1" state, from the decoder 84 is utilized to set the K input of the flip-flop 98 so that, instead of being decremented by two counts relative to the control register during each counting cycle, the pulse width register 85 is now decremented by nine counts during each counting cycle. This start-up phase can only be terminated by resetting the start-up flip-flop 114 and, as will subsequently become apparent, this will only occur after two drops have been detected.

When a drop is detected, flip-flop 118 is set "true" immediately and it will then set the flip-flop 119 "true", in the manner previously described for normal operation. The Q output of the flip-flop 119 is directed not only over line 125 to "reset" the flip-flop 118, but is also directed over line 151 as an input to each of a pair of AND gates 153 and 154. The other inputs to the AND gate 153 are the "zero" state of the pulse width register from the decoder 86, over line 155, and the Q output of the start-up flip-flop 114, over line 156. Hence, the gate 153 will only be enabled when the system is in the start-up phase, a drop has been received, and the pulse width register 85 has been counted to "zero". Therefore, when the first drop is detected, and the pulse width register goes through "zero", the output of the gate 153 sets the J input of the flip-flop 140 so that, on the next CLK pulse the flip-flop 140 will be set "true".

The flip-flop 119 will be "reset" as the pulse width register 85 counts past "20", to remove the "true" output over line 151 and thereby disable the gate 153. Nothing further happens in the start-up subsystem until a second drop is detected and the flip-flop 119 is again set "true". At this time, the output of the AND gate 154 will go "true" on line 161 when the pulse width register 85 counts through "zero", since both of the inputs to gate 154 over lines 151 and 158 will then be "true", and the Q output of the flip-flop 140, over line 159, will also be "true" (from the counting cycle when the first drop was detected), thus providing the third enabling input to the AND gate 154. When the AND gate 154 is enabled, its "true" output resets flip-flop 140 and the start-up flip-flop 114 on the next CLK pulse. This results in a "true" $\overline{Q}$ output from the flip-flop 114, thus disabling the gate 105 and enabling the gate 106, so that the system exits from the start-up phase and resumes normal operation in decrementing the pulse width register 83 by two counts during each counting cycle.

During the start-up phase, the "true" state of the Q output from the start-up flip-flop 114 is directed, over line 157, to the rate multiplier 42 (FIG. 4a) to temporarily override the rate selector switches 42a, and internally force the pulse generation subsystem to a predetermined pulse rate most suitable for initial adjustment of pulse width. This arrangement insures pulse width adjustment at an initial pulse rate which is neither too slow nor too fast, considering the loop gain of the overall system. When the start-up phase is terminated, the Q output of the flip-flop 114 will go "false", and the rate selector switches 42a will resume normal rate determination control over the rate multiplier 42a.

It will be apparent to those of ordinary skill in the art that, during the start-up phase, the input over line 157 obviously gates "off" the normal rate selector switch inputs and gates "in" the prescribed start-up phase rate setting. For purposes of simplicity, the specific gate configuration, which may assume a wide variety of conventional logic configurations, has been omitted.

The output pulse control subsystem will be next described. The output pulses are generated over line 72 by the "true" output of an output pulse control flip-flop 162 which is normally "reset" when the system is first initialized, over line 163.

The J input of the flip-flop 162 is under the control of an AND gate 165 which, in turn, has three inputs. One input to the gate 165, over line 166, is the DRZ signal. The other two inputs to the AND gate 165, over lines 167 and 168, are lines which are normally "true" but potentially disabling, the inputs over lines 167 and 168 being from the alarms subsystem which will be subsequently described. Hence, under normal conditions, each time a DRZ pulse appears on line 166, the J input of the flip-flop 162 will be "set" and, on the next CLK pulse, the flip-flop 162 will go "true". This initiates the output pulse from the system over line 70 (in the "pump" mode) or over line 73 (in the "controller" mode).

The output pulse to the output control device can only be terminated by resetting the flip-flop 162. In this regard, the K input of the flip-flop 162 is controlled by an OR gate 170 having two inputs, one input over line 171 representing the "zero" state of the pulse width register 85 from the decoder 86, the other input over line 172 being the duty cycle limitation signal at the output of the OR gate 51.

Hence, each output pulse over line 72 is initiated by a DRZ pulse, and the pulse is terminated whenever the pulse width register 85 overflows to its "zero state", thus determining the pulse width of the output pulse. If, on the other hand, a pulse width is called for beyond the duty cycle limitation, then, before the pulse width register 85 overflows, the line 172 will go "true", setting the K input of the flip-flop 162. On the next CLK pulse, the flip-flop 162 will be "reset" to terminate the output pulse on line 72 and provide an instantaneous limitation on the mechanical output from the overall system.

While the output pulse lines 70 and 73 are shown as directly driving the particular electromechanical output control device utilized, it will be appreciated that, depending upon the characteristics of the particular mechanical output, it may be necessary to introduce appropriate delays prior to actual energization by the output pulses. For example, in the "pump" mode, the pump motor is normally shut off between output pulses. Therefore, rather than enabling the stepping motor driver 71 immediately by the output control signal, a delay of a few clock pulses is introduced to allow the power signal to the motor to come up to full level before actually allowing stepping motor pulses to be applied. Hence, a delay of a few milliseconds, while not actually shown in the drawing of the overall system, may be conveniently introduced in any appropriate manner, as by a suitable one-shot, where needed.

The alarms subsystem is next described. An AND gate 175 controls the high level alarm, that is, the alarm response to a requirement for too wide an output pulse. One input to the AND gate 175 is the DRZ pulse on line 176 which also starts every counting cycle and every output pulse to the output control device. Hence the AND gate 175 can only be enabled during the one clock period duration of the DRZ pulse, so that each time the DRZ pulse appears at the input of the gate 175, the system is being tested for the status of the other input lines to that gate. If all three other input lines to the gate 175 are "true", then an output from gate 175 is provided which is passed by the OR gate 180 to set the alarm flip-flop 145 which, on the next CLK pulse, goes "true" to energize the alarm display 181.

A second input to the gate 175, over line 177, comes from the $\overline{Q}$ output of a flip-flop 182, so that flip-flop 182 must be in the "reset" condition for the gate input line 177 to be "true". A third input to the gate 175, over line 178, is from the 768-1023 output of the pulse width register decoder 86, which is "true" only when the pulse width register 85 is in the last 25 percent of its upper counting range (indicating a very narrow pulse width). The fourth input to the gate 175, over line 179, is the $\overline{Q}$ output of a flip-flop 183, so that flip-flop 183 must also be "false", as in the case of the flip-flop 182, in order to enable the gate 175.

The only time that the flip-flop 183 can be "false" when a DRZ pulse occurs, is if flip-flop 183 has been "reset" on the previous counting cycle. In this regard, the flip-flop 183 getw either "set" or "reset" after every DRZ pulse, so that the flip-flop 183 is tested at the start of every counting cycle. The J input of the flip-flop 183 is controlled by an input AND gate 185, and the K input of the flip-flop 183 is controlled by an input AND gate 186. Each of these gates receives the DRZ pulse as an input over line 187.

The second input to the gate 185, over line 190, is the 512-1023 high order flip-flop output of the pulse width register 85 from the decoder 86. This same output on line 190 is inverted and then directed as the second input to the gate 186. Therefore, if the pulse width register 85 has come to rest in a high count state during the last counting cycle, then the gate 185 will be enabled on the next DRZ pulse to set the flip-flop 183 to its "true" state on the very next CLK pulse. If, on the other hand, the pulse width register 85 ends the preceding counting cycle with a count below "512", then the gate 186 will go "true" on the next DRZ pulse to "reset" the flip-flop 183.

Hence, if a very wide output is produced on the preceding counting cycle (represented by a low count in the pulse width register 85), the flip-flop 183 will be "reset" on the next counting cycle and its $\overline{Q}$ output will go "true". In contrast, a narrower pulse (pulse width register count of "512" or more) in the preceding counting cycle will set the flip-flop 183 so that its Q output is "true". Thus, the flip-flop 183 essentially remembers whether the system had a wide pulse or a narrow pulse on the immediately proceding counting cycle and is used throughout the alarms subsystem for this purpose.

Asseming the output pulses are getting longer and longer with each counting cycle, the flip-flop 183 will likewise be reset on each counting cycle to maintain its $\overline{Q}$ output "true". When a counting cycle is finally reached where the pulse width register 85 just barely underflows, the output line 768-1023 from the decoder 86 will provide a "true" output, over line 178, to the AND gate 175. This represents a condition where a very wide output pulse in one counting cycle is immediately followed by an extremely narrow output pulse on the very next counting cycle, indicating that the pulse width register 85 has underflowed.

Since the flip-flop 183 had been "reset" every time a long output pulse occurred, it is still "reset" from the previous counting cycle and, with the 768-1023 line "true", the AND gate 175 will be enabled if the $\overline{Q}$ output from the flip-flop 182 is also "true". The latter flip-flop 182 is "reset" when the system is turned on and is, therefore, normally "false" so that its $\overline{Q}$ output on line 177 will also normally be "true". It will be apparent, therefore, that whenever a wide pulse is followed by an extremely narrow pulse, the AND gate 175 will be enabled and the system will go into high level alarm.

As will subsequently become apparent, the flip-flop 182 has as its function to remember (in the "pump" mode of operation) that a very wide pulse width has been produced after a very narrow pulse width, and that it is not yet desired to go into low level alarm because of the capability of the pump for normal operation in the negative pulse width region of the pulse width register 85.

An AND gate 195 sets the controller low level alarm. One input to the gate 195, over line 196, is the DRZ signal at the beginning of each counting cycle. A second input, over line 197, is the Q output of the flip-flop 183 (representing a relatively short output pulse on the preceding counting cycle). A third input, over line 198, is the 0-255 state from the pulse width register decoder 86, indicating that the present pulse being called for has a very long pulse period. A fourth input to the gate 195, over line 199, indicates that the system has been set by the jumper 53 (FIG. 4a) to operate in the "controller" mode. The fifth input to the gate 195, over line 201, is the $\overline{Q}$ output of the start-up flip-flop 114 which indicates, when the line 201 is "true", that the system is out of the start-up phase. This prevents the controller from going into alarm during the start-up phase, since the system normally starts out with extremely narrow pulses (both registers having been reset to "zero" initially).

Hence, the input lines 199 and 201 to the AND gate 195 will always be "true" in normal operation (outside of the start-up phase). Therefore, whenever a very narrow pulse on the immediately preceding counting cycle is being followed by an extremely wide pulse (a pulse width register count of 255 or less), the AND gate 195 will be enabled to pass the very next DRZ and thereby trigger the controller low level alarm through the OR gate 180, to "set" the alarm flip-flop 145.

The transition from a narrow pulse to an extremely wide pulse indicates that the pulse width register has underflowed which means, in the "controller" mode, that the system is incapable of producing pulses sufficiently narrow to arrest further fluid flow, e.g., either the controller is incapable of clamping off the feeding tube or a leak exists, so it is desirable to go into the alarm state.

The pump low level alarm is controlled by an AND gate 204. The pump low level alarm will not be triggered merely by underflow of the pulse width register 83 (negative pulse width), since this may still be normal operation in the "pump" mode. Rather, it is intended that the pump low level alarm will be triggered when the pulse width called for in the "pump" mode of operation has exceeded a negative pulse width requirment of 25 percent, i.e., the virtual pulse width has gone from something more than 75 percent on the previous counting cycle to less than 75 percent of the miximum pulse width on the present counting cycle. The term "virtual pulse width" is utilized because, as will become apparent, the actual output pulse to the output control device (the stepping motor driver 71) is actually gated off when the pulse width register 85 is in the negative region.

The sequence of alarm conditions for the pump low level alarm is a very narrow pulse, followed by a very wide pulse (underflow of the pulse width register 85 into the negative region) followed immediately by a reduction in that very wide pulse width to a pulse width just below 75 percent of the maximum pulse width. Essentially, this is very much like the controller low level alarm except the low level boundary is at minus 25 percent of the pulse width register rather than at the zero level of the pulse width register, thus providing enhanced dynamic range for the "pump" mode of operation.

The reason for going into pump low level alarm under the aforedescribed conditions is that a burst of drops from the pump may occur which temporarily may drive the pulse width register 85 into the negative region, all as part of the normal operation of the pump. However, in such normal operation, the pump will gradually return to a narrow pulse width in the positive range of the pulse width register. If, on the other hand, the pulse width register 85 is continually incremented by more and more drops calling for even larger negative pulse width on a virtual basis, this indicates that, even with no mechanical output from the pump (the motor is gated off when the pulse width register is in the negative region) additional drop flow is being produced, and an alarm state should be generated.

The flip-flop 182 gets "set" by the same conditions that would trigger a low level alarm in the "controller" mode of operation. In this regard, the J input of the flip-flop 182 is controlled by an AND gate 205 which receives as one input, over line 206, the Q output of the flip-flop 183 and, as a second input over line 207, the 0-255 output from the pulse width register decoder 86. The third input to the AND gate 205, over line 208, is the DRZ signal.

Hence, if there was a very narrow pulse width on preceding counting cycle, the Q output of the flip-flop 183 will be "true". If, in addition, a very wide pulse width is being called for on the next counting cycle, the 0-255 decoder output line from the pulse width register 85 will also be "true" so that, on the next DRZ pulse, the gate 205 will be enabled, the J input of the flip-flop 182 will be "set" and, on the very next CLK pulse, the Q output from the flip-flop 182 will go "true" on line 209 to the gate 204.

The "true" output of the gate 205 is also directed, over line 210, through an inverter 212 (FIG. 4a) to produce a "false" output on line 168 and disable the input AND gate 165 which controls the J input of the output pulse control flip-flop 162. This prevents any output pulses from being directed to the output control device whenever the pulse width register is starting to operate in the negative pulse width region.

The AND gate 214 controls the K input of the flip-flop 182. One input to the gate 214 is the DRZ signal, while the second input to the gate, over line 215, is the 768-1023 output line from the pulse width register decoder 86. Hence, the output of the gate 214 will remain "false" as long as wide pulse widths continue to be generated.

It will be apparent, from the foregoing, that the flip-flop 182 gets "set" whenever a narrow pulse width becomes a very wide pulse width (negative pulse width region), and the flip-flop 182 only get "reset" again in going from a very wide pulse width to a very narrow pulse width. As long as the system remains in the very wide pulse width region, the flip-flop 182 remains set "true". In switching back to narrow pulse width operation, the $\overline{Q}$ output of the flip-flop 182 is still "false" when the very next DRZ pulse occurs and prevents the high level alarm (the input over line 177 to the AND gate 175) from being activated because of the previous operation in the wide pulse width region.

Another input to the pump low level alarm gate 204, over line 216, is the 256-511 output line from the decoder 86 of the pulse width register 85, which represents a pulse width from one-half to three-fourths of the maximum pulse width.

The AND gate 204 is only enabled when a short pulse width is followed by a very wide pulse width which ultimately drops down to a pulse width of less than 75 percent of the maximum pulse width. This incicates that drop flow keeps coming, thereby continually reducing the pulse width more and more, until a negative pulse width beyond 25 percent is exceeded, which means that the system cannot prevent flow even when the pump is turned off, and thus indicating an alarm state.

Again, the sequence for pump low-level alarm must be a short pulse width followed by a long pulse width, followed further by an attempt by the system to reduce the pulse width below 75 percent. Under these conditions, flip-flop 182 is "true", and the pulse width register is into the second 25 percent of its count range (256-511) so that line 216 is also "true" and, on the next DRZ pulse, the gate 204 will be enabled to trigger an alarm state.

The $\overline{Q}$ output of the flip-flop 182 is also directed over the line 167 as an input to the AND gate 165 (FIG. 4a) and, since the $\overline{Q}$ output is normally "true", it typically does not affect the generation of the output pulse by the flip-flop 162, except when the flip-flop 182 is set "true" indicating operation in the negative region of the pulse width register 85.

Once operation in the "pump" mode has gone into the negative pulse width region of the pulse width register 85, the system must be capable of coming out of the potential alarm state, operating with a narrow pulse width in the positive region of the pulse width register 85, and be prepared to again respond to an improper pulse width sequence calling for excessive negative pulse width. In this regard, upon the elimination of the transitory condition calling for negative pulse width, the system should normally begin to produce very narrow pulse widths, and the 768-1023 output line from the pulse width register decoder 86 should go "true", thus enabling the gate 214 on the next DRZ pulse and causing the flip-flop 182 to be "reset" on the next CLK pulse. This output condition will not cause the high level alarm (AND gate 175) to be enabled since the $\overline{Q}$ output of the flip-flop 183 is also one of the inputs to the gate 175, will now be "false".

During initial start-up of the overall system, the flip-flop 182 is "reset" and the flip-flop 183 is set "true". The reason for this is that, in the start-up phase of operation, which starts out with a very wide pulse period, (the pulse width register 85 is at "0") the flip-flops 183 and 182 must be initially set to indicate the appearance of having received a narrow pulse width on a fictitous preceding counting cycle. This will cause flip-flop 182 to be set "true" by the very first DRZ pulse and also disable gate 165 which prevents the first pulse, which is a very wide pulse, from being directed to the output control device. The second output pulse, now a very short pulse, is prevented from activating the high level alarm because the flip-flop 182 is still "true" and is only "reset" after the second output pulse has been initiated by a DRZ pulse. The sequence of simulated short pulse period and an initial wide pulse period would also normally activate the low level alarm in the "controller mode". However, this is prevented by the signal on line 201 which disables the gate 195 during the start-up phase.

The function of the "no-drop" alarm produced by a "true" output from the OR gate 225 is to count the number of DRZ pulses, i.e., the number of counting cycles initiated in the digital memory subsystem, and to trigger an alarm state in the event no drops are detected within a prescribed number of such counting cycles.

The DRZ pulses are directed over line 226 as input to a counter 227, typically a counter with a range of $2^7$. The output of the counter 227 is decoded via a decoder 228 which has two output lines, one output line representing a count of 64 DRZ pulses, the other line representing a count of 96 DRZ pulses. The counter 227 is "reset", each time a drop is detected, by a "true" output on line 230 representing the state of the flip-flop 119 in the control subsystem. It will be recalled that the latter flip-flop 119 gets set "true" during the counting cycle following detection of a drop.

The "64" output line from the decoder 228 is directed as one input to an AND gate 232 which has a second input, over line 233, from the Q output of the start-up flip-flop 114. Hence, during normal operation, when the system is out of the start-up phase, a count of 64 DRZ pulses received, without any drops being detected, will cause the gate 232 to go "true", and thereby trigger an alarm state through the OR gates 225 and 180.

When the system is still operating in the start-up phase, it may take more counting cycles to generate the first drop, since the system starts out with a very narrow pulse width. Therefore, when the system is in the start-up phase, the gate 232 is disabled, and the "96" output line from the decorder 228 is used to indicate that 96 counting cycles have occurred without the detection of a drop, in order to trigger the no-drop alarm state.

A "no action" alarm is also included in the alarm subsystem and gets activated if there are no drops or output pulses from the system occurring for any period of six minutes.

The "no action" alarm includes a flip-flop 235 which resets a counter 236 (typically a $2^7$ counter) each time the flip-flop is set "true". The counter 236 is "reset" through a pulse gate indicated by a capacitor 237a and resistor 237b. The pulse gate is actually a differentiator which receives the Q output level of the flip-flop 235 and converts it to a pulse capable of resetting the counter 236. The flip-flop 235 is, in turn, set to its "true" state over the line 238 whenever the output flip-flop 162 (FIG. 4a) goes "true". The output on line 238 is also coupled through a pulse gate consisting of a capacitor 239a and resistor 239b, so that the pulse which sets the flip-flop 235 only occurs when the output flip-flop 162 is going from its "false" state to its "true" state. The flip-flop 235 is "reset" by an input over line 241 from the drop detector 115 (FIG. 4b) each time a drop is detected. Again, the output from the drop detector 115 is coupled to the "reset" input of the flip-flop 235 through a pulse gate consisting of a capacitor 242a and a resistor 242b.

If output pulses are initially produced and then cease to be produced by the output flip-flop 162, there will be no pulses at the Q output of the flip-flop 235, since there is no change in the Q output of the flip-flop and only a change in output will be passed by the gate. Similarly, if no drops occur, no pulses will occur at the output of the flip-flop 235, since a drop is required to "reset" the flip-flop 235 before the flip-flop can be "set" again, and a pulse output will only be produced at the Q output of the flip-flop in going from the "reset" state to the "set"-state.

Hence, if the flip-flop 235 keeps getting set from the output flip-flop 162, without any drops being detected, the flip-flop 235 will already have been in the "set" state and no transistion pulses will be generated at the Q output of the flip-flop 235 and, accordingly, the counter 236 will not be "reset". Thus, it will be apparent that the presence of both drops and output pulses are necessary to generate pulse output from the flip-flop 235 to reset the counter 236. If neither drops nor output pulses occur for approximately six minutes, the counter 236 will be countered up by an oscillator 245 over line 246. When a decoder 247 produces an output over line 248 indicating that counter 236 has counted up 64 clock periods from the oscillator 245, a six minute "no action" alarm will be generated by the output of the OR gate 180.

It will be apparent that 64 periods, at 5.6 seconds for each period, yields a time interval of approximately 6 minutes. The reason for selecting the six minute time interval is that, at very low pumping rates, it can actually take as long as a period slightly less than 6 minutes between a pair of drops, and it is desired to avoid the alarm state for this condition of operation.

The "no action" alarm will also be triggered if the operator inadvertently selects a zero drop rate. Under those conditions, no DRZ pulses will be produced, and therefore, the "no-drop" alarm condition monitored by the OR gate 225 will be ineffective. However, the "no-action" alarm will be triggered after 6 minutes.

The visual pulse width indication subsystem is next described. The visual pulse width indication subsystem is used only in connection with those output control devices which depend on gravity induced hydrostatic pressure levels, such as controllers rather than pumps.

A red light driver circuit 251 and a green light driver circuit 252 are controlled by their own flip-flops 253 and 254, respectively. The J and K inputs to these flip-flops 253, 254 are controlled by four AND gates. An AND gate 255 controls the J input of the flip-flop 253, the K input of that flip-flop being controlled by an AND gate 256. The J input of the flip-flop 254 is controlled by an AND gate 258, the K input of that flip-flop being controlled by an AND gate 257.

All four AND gates 255, 256, 257 and 258 have as one input the DRZ signal, over line 187. Hence, the visual pulse width indication subsystem is only "set" or "reset" at the beginning of a counting cycle initiated by a DRZ pulse. The subsystem thus indicates between DRZ pulses where the subsystem had been set on the last DRZ pulse.

When the system first starts out (power turned on) the red light flip-flop 253 is "reset" while the green light flip-flop 254 is set "true" over line 260. Hence, on start-up, the green light will go on immediately. When the first DRZ pulse comes along after such initialization, the pulse width register 85 has been initially set to the "zero" state, so that the 0-276 output line from the decoder 86 will be "true". This produces a "true" input over line 262 to AND gate 255 and is inverted by an inverter 261 to provide a "false" input over line 263 to the AND gate 256. Hence, the AND gate 255 will be enabled, at the DRZ pulse, to "set" the J input of the flip-flop 253 which, on the next CLK pulse, will go "true" and turn on the red light. Meanwhile, on the first DRZ pulse, with the pulse width register 85 at "zero", the 640-1023 line out of the decoder 86 will be "false". This produces a "false" output on line 265 to the AND gate 258 and is inverted by an inverter 264 to produce a "true" input over line 266 to the gate 257. Hence, the green light flip-flop 254 is "reset" by the first DRZ pulse and, as the red light turns on, the green light momentarily turns off.

On the second DRZ pulse, the pulse width register 85 will now have nine counts less (start-up phase) than it had before, so that the output line 640-1023 from the decoder 86 will now go "true", resulting in enabling of the AND gate 258 and disabling of the gate 257, which "sets" the flip-flop 254 and turns on the green light. At the same time, the 0-766 output line from the decoder 86 goes "false", which disables the gate 255 and enables the gate 256, so that the DRZ pulse "resets" the flip-flop 253 and turns off the red light.

The visual pulse width indication subsystem remains in the state with the green light on and the red light off until the pulse width is sufficiently wide so that the 0-766 line out of the decoder 86 again goes "true" and enables the gate 255 to "set" the red light flip-flop 253 and turn on the red light. Since the 640-1023 output line from the decoder 86 is still "true", the green light flip-flop 254 has not yet been "reset". Under these conditions, both the red light and the green light will be turned on.

If the count in the pulse width register 85 is further reduced below a count of 640, then the output line 640-1023 from the decoder 86 will go "false", gate 258 will be disabled, gate 257 will be enabled, and the green light flip-flop 254 will be "reset" to turn off the green light. The red light flip-flop 253 will now remain set to its "true" state, with the red light on, all the way down to a "zero" count in the pulse width register 85, indicating very wide pulses.

Hence, the visual pulse width indication system enables ready observance by medical personnel of the output pulse width range of the fluid flow control system so that, if excessively wide or excessively narrow pulses are being produced, the administration set can be adjusted, as by raising or lowering the bottle, to bring the output pulse width into the optimum operating range for the controller.

The new and improved fluid flow control system of the present invention is extremely accurate, reliable and easy to use. The system provides enhanced digital precision in selecting and maintaining drop flow rates throughout a wide range, and the system is quick to inform medical personnel of any indications which might pose a hazard to the patient. System testing and calibration is considerably simplified and is essentially accomplished merely by checking the clock 40. Hence, the system of the present invention minimizes the time-consuming and error-prone aspects of human monitoring flow rate adjustment, provides substantial improvement in economy, adaptability of a single system to a variety of different mechanical output control devices, and enhanced reliability, stability and accuracy over previous automatic control systems.

It will be apparent from the foregoing that, while particular forms of the invention have been illustrated and described, various modifications can be made without departing from the spirit and scope of the invention.

I claim:

1. In a system for parenteral administration of liquids at desired drop flow rates through a feeding tube from a liquid source to a patient, the combination comprising:
   electromechanical output control means for manipulating the feeding tube to vary the flow of liquid in the feeding tube;
   electrical pulsing means for providing output pulses to operate said output control means, said output control means being active during the periods between said output pulses in a pulse train, said output pulses being at a substantially higher frequency than the desired drop flow rate frequency; and
   digital memory and timing means for automatically predetermining and varying the pulse width of said output pulses operating said control means, to achieve the desired drop flow rate.

2. A system as set forth in claim 1, wherein said digital memory and timing means includes at least one counter.

3. A system as set forth in claim 2, and further including:
   means for providing a negative pulse width by overflow of said counter through successive incrementing of said counter when a plurality of drops have been detected in rapid succession.

4. A system as set forth in claim 1, wherein said digital memory and timing means includes a pair of digital counters.

5. A system as set forth in claim 1, wherein said digital memory and timing means includes a digital counter which undergoes successive counting cycles, a single counting cycle for each of said output pulses produced by said pulsing means, the count state of said counter at the beginning of each counting cycle determining the pulse width of the corresponding output pulse produced during that counting cycle.

6. A system as set forth in claim 5, and further including:
   means for decrementing said counter by a first prescribed number of counts during each of said counting cycles, and for incrementing said counter by a second prescribed number of counts only during a counting cycle after a drop of liquid flow has been detected.

7. A system as set forth in claim 6, wherein the ratio of said second prescribed number of counts to said first prescribed number of counts is a predetermined value.

8. A system as set forth in claim 7, wherein said ratio is the same as the ratio of the frequency of said output pulses produced by said pulsing means to the desired drop flow rate frequency.

9. A system as set forth in claim 7, wherein the frequency of said output pulses is a high, non-integral multiple of the desired drop flow rate.

10. A system as set forth in claim 9, wherein said ratio is 10½.

11. Apparatus as set forth in claim 1, and further comprising:
    means responsive to a predetermined sequence of states of said digital memory means for generating an alarm state.

12. Apparatus as set forth in claim 1, and further comprising:
    means responsive to a predetermined sequence of pulse widths of said output pulses for generating an alarm state.

13. Apparatus as set forth in claim 1, and further comprising:
    means responsive to a lack of detection of flow of liquid in said feeding tube within a prescribed period of time for generating an alarm state.

14. A system as set forth in claim 1, wherein said digital memory means further comprises:
    a first digital counter; and
    a second digital counter having a counting cycle under the control of said first counter.

15. Apparatus as set forth in claim 14, including means responsive to a prescribed sequence of states of said second counter for generating an alarm state.

16. A system as set forth in claim 1, and further comprising:
    means for selectively overriding said digital memory and timing means for imposing a duty cycle limitation upon said pulse width.

17. A system as set forth in claim 1, and further comprising:
    visual display means for indicating the range of magnitudes of the pulse widths of said output pulses.

18. Apparatus as set forth in claim 17, wherein said visual display means includes a pair of lights which are energized in predetermined combinations to indicate a plurality of pulse width ranges of operation.

19. A system as set forth in claim 1, and further comprising:
    means for temporarily overriding normal control of said pulsing means and setting said pulsing means to a prescribed pulse rate during predetermined periods of operation.

20. In a system for parenteral administration of liquids at a desired drop flow rate through a feeding tube from a liquid source to a patient, the combination comprising:
    output control means for determining the rate of drop flow of liquid in the feeding tube;
    electrical pulsing means for providing successive output pulses to said output control means, said output control means being inactive during the periods between said output pulses in a pulse train, said output pulses being at a substantially higher frequency than the desired drop flow rate frequency; and
    counting means for varying the pulse width of each of said output pulses, to achieve the desired drop flow rate.

21. A system as set forth in claim 20, wherein said counting means comprises:
    a first counter; and
    a second counter having a counting cycle under the control of said first counter.

22. A system as set forth in claim 21, and further comprising:
    means responsive to a sequence of states of said second counter for generating an alarm state.

23. A system as set forth in claim 21, and further comprising:
    means responsive to a lack of detection of fluid flow within a prescribed period of time for generating an alarm state.

24. A system as set forth in claim 21, and further comprising:

means responsive to the lack of detection of drops within a prescribed period of time for generating an alarm state.

25. A system as set forth in claim 24, wherein said time is a function of the number of pulses generated by said electrical pulsing means.

26. A system as set forth in claim 24, wherein said time is a function of the lack of occurrence of drops or output pulses for a prescribed period of time.

27. A system as set forth in claim 21, wherein said first and said second counters undergo successive counting cycles, a single counting cycle for each of said output pulses produced by said pulsing means, the count state of said second counter at the beginning of each counting cycle determining the pulse width of the corresponding output pulse produced during that counting cycle.

28. A system as set forth in claim 27, and further including:
means for decrementing said second counter relative to said first counter by a first prescribed number of counts during each of said counting cycles, and for incrementing said second counter relative to said first counter by a second prescribed number of counts only during a counting cycle after a drop has been detected.

29. A system as set forth in claim 28, and further comprising:
means responsive to a predetermined sequence of pulse widths for generating an alarm state.

30. A system as set forth in claim 29, wherein said predetermined sequence of pulse widths is a narrow pulse width of prescribed magnitude followed by a wide pulse width of prescribed magnitude.

31. A system as set forth in claim 29, wherein said predetermined sequence of pulse widths is a wide pulse width of prescribed magnitude followed by a narrow pulse width of prescribed magnitude.

32. A system as set forth in claim 29, wherein said predetermined sequence of pulse widths is a narrow pulse width of prescribed magnitude followed by a wide pulse width of prescribed magnitude, followed by a narrow pulse width of prescribed magnitude induced by further and successive incrementing rather than further successive decrementing of said second counter.

33. A system as set forth in claim 28, wherein the ratio of said second prescribed number of counts to said first prescribed number of counts is a predetermined value.

34. A system as set forth in claim 33, wherein said ratio is the same as the ratio of the frequency of said output pulses to the desired drop flow rate frequency.

35. A system as set forth in claim 34, wherein said ratio is 10½.

36. A system as set forth in claim 28, and further comprising:
start-up means for preventing normal system response to a predetermined number of initial drops of liquid flow in the feeding tube.

37. A system as set forth in claim 25, and further including:
means for increasing said first prescribed number of counts by which said counter is decremented during each of said counting cycles to a larger number for each counting cycle which occurs during predetermined periods of operation.

38. A system as set forth in claim 37, and further comprising:
means for temporarily overriding normal control of said pulsing means and setting said pulsing means to a prescribed pulse rate during said predetermined periods of operation.

39. A system as set forth in claim 28 and further including;
means for providing a negative pulse width by overflow of said second counter as a result of successive incrementing of said second counter when a plurality of drops have been detected in rapid succession.

40. In a system for parenteral administration of liquids at a desired drop flow rate via a feeding tube from a liquid source to a patient, the combination comprising:
electromechanical output control means for varying fluid flow in the feeding tube;
electrical pulsing means for providing output pulses to said output control means, said output control means being inactive during the periods between said output pulses in a pulse train, said output pulses being at a substantially higher frequency than the desired drop flow rate frequency;
digital pulse generation and rate determination means for generating command pulses to selectively control the frequency of said output pulses and the time of initiation of each of said output pulses; and
digital memory means for automatically determining the pulse width of each of said output pulses.

41. Apparatus as set forth in claim 40, and further comprising:
means responsive to the lack of detection of drop flow within the period of time determined by a prescribed number of pulses generated by said pulse generation and rate determination means.

42. Apparatus as set forth in claim 40, wherein said pulse width is increased with each command pulse produced by said pulse generation and rate determination means, and said pulse width is decreased with each drop detected.

43. Apparatus as set forth in claim 42, and further comprising:
means responsive to the lack of detection of drop flow within the period of time determined by a prescribed number of said command pulses generated by said pulse generation and rate determination means for generating an alarm state.

44. Apparatus as set forth in claim 40, and further comprising:
means responsive to excessive pulse width for generating an alarm state.

45. Apparatus as set forth in claim 40, and further comprising:
means responsive to a predetermined reduced pulse width for generating an alarm state.

46. Apparatus as set forth in claim 40, and further comprising:
means responsive to a predetermined sequence of pulse widths for generating an alarm state.

47. Apparatus as set forth in claim 46, wherein said predetermined sequence of pulse widths is a narrow pulse width of prescribed magnitude followed by a wide pulse width of prescribed magnitude.

48. Apparatus as set forth in claim 46, wherein said predetermined sequence of pulse widths is a narrow pulse width of prescribed magnitude followed by a wide pulse width of prescribed magnitude, followed by a narrow pulse width of prescribed magnitude.

49. Apparatus as set forth in claim 46, wherein said predetermined sequence of pulse widths is a wide pulse width of prescribed magnitude followed by a narrow pulse width of prescribed magnitude.

50. Apparatus as set forth in claim 40, and further comprising:
means responsive to a predetermined sequence of pulse widths in prescribed ranges of magnitude for generating an alarm state.

51. Apparatus as set forth in claim 40, and further comprising:
means responsive to a predetermined sequence of states of said digital memory means for generating an alarm state.

52. Apparatus as set forth in claim 40, and further comprising:
means responsive to the lack of detection of drop flow within a prescribed period of time for generating an alarm state.

53. Apparatus as set forth in claim 52, wherein said time is a function of the number of said command pulses generated by said pulse generation and rate determination means.

54. Apparatus as set forth in claim 52, wherein said time is a function of the lack of occurrence of drops or output pulses for a prescribed period of time.

55. Apparatus as set forth in claim 40, and further comprising:
digital start-up subsystem means for preventing normal system response to a predetermined number of initial drops.

56. A system as set forth in claim 40, and further comprising:
means for temporarily overriding normal control and setting said pulse generation and rate determination means to a prescribed pulse rate during predetermined periods of operation.

57. In a parenteral infusion system, the combination comprising:
output means for controlling fluid flow in a feeding tube;
electrical pulsing means for providing output pulses to said output means, said output means being inactive during the periods between said output pulses in a pulse train;
digital counting means for predetermining and varying the pulse width of said output pulses; and
visual display means indicating the range of magnitudes of the pulse widths of said output pulses.

58. Apparatus as set forth in claim 57, wherein said visual display means includes a pair of lights which are selectively energized to indicate a plurality of pulse width magnitude ranges of operation.

59. In an I.V. system for producing output drive pulses to drive an electromechanical output control means for varying fluid flow in a feeding tube, the combination comprising:
electrical pulsing means for providing output pulses;
a pair of counters for determining the pulse width of each of said output pulses; and
means to increment or decrement the relative count between said counters depending upon detection or nondetection of drops.

60. Apparatus as set forth in claim 59, wherein said pulse width is increased during each period between initiation of successive of said output pulses and decreased with each drop detected.

61. Apparatus as set forth in claim 60, and further comprising:
means for generating an alarm state in said system in response to the detection of lack of fluid flow in said system.

62. Apparatus as set forth in claim 60, and further comprising:
means for generating an alarm state in said system in response to the detection of excessive pulse width in said system.

63. Apparatus as set forth in claim 60, and further comprising:
means for generating an alarm state in said system in response to the detection of reduced pulse width of prescribed magnitude in said system.

64. In a system for parenteral administration of liquid via a feeding tube from a liquid source to a patient, the combination comprising:
output control means for regulating fluid flow in the feeding tube;
electrical pulsing means for controlling the generation of output pulses to incrementally energize said output control means, said output control means being inactive during the periods between said output pulses in a pulse train;
digital memory and timing means for predetermining and varying the pulse width of said output pulses energizing said output means;
flow monitoring means for monitoring liquid flow in the administration system; and
digital means responsive to said electrical pulsing means and said flow monitoring means for indicating a lack of flow within a time period determined by a specified number of said pulses.

65. In a system for parenteral administration of liquid via a feeding tube from a liquid source to a patient, the combination comprising:
output control means for regulating fluid flow in the feeding tube;
electrical pulsing means for generating output pulses to incrementally energize said output control means, said output control means being inactive during the periods between said output pulses in a pulse train;
digital memory and timing means for predetermining and varying the pulse width of said output pulses energizing said output means;
flow monitoring means for monitoring liquid flow in the administration system; and
digital means responsive to said pulsing means and said flow monitoring means for indicating a lack of either flow or output pulses within a prescribed time period.

66. In a system for parenteral administration of liquid via a feeding tube from a liquid source to a patient, the combination comprising:
output control means for regulating fluid flow in the feeding tube;
electrical pulsing means for generating output pulses to incrementally energize said control means;
means for varying the pulse width of said output pulses energizing said output means;
flow monitoring means for monitoring liquid flow in the administration system;
pulse width monitoring means; and
means responsive to said pulse width monitoring means for indicating the occurrence of a prescribed nontolerated sequence of pulse widths.

67. In a system for parenteral administration of liquid via a feeding tube from a liquid source to a patient, the combination comprising:
electromechanical output means;
driving means for driving said output means;

an open loop digital control means for digitally establishing the frequency of output pulses electrically energizing said driving means, said driving means being inactive during the periods between said output pulses in a pulse train; and a closed loop digital memory control means for digitally predetermining and varying the pulse width of said output pulses to said driver means.

68. A system as set forth in claim 67, wherein said open loop control means includes:
digital pulse generation means; and
digital rate determination means.

69. A system as set forth in claim 67, wherein said closed loop digital control means includes a digital counter.

70. A system as set forth in claim 67, wherein said driving means is an electrical stepping motor, and said electromechanical output means is a pump.

71. A combination as set forth in claim 67, wherein said electromechanical output means is a feeding tube pincher, and said driving means is an electromagnetic actuator.

72. In a system for parenteral administration of liquid via a feeding tube from a liquid source to a patient, apparatus comprising:
positive pressure infusion pump means;
digital rate setting means for generating an electrical pulse train at a frequency proportional to desired liquid flow rate;
stepping motor means for driving said pump means, said motor means being inactive during the periods between pulses in said pulse train;
digital flow monitoring means for monitoring liquid flow induced by said pump means; and
digital memory means responsive to both said digital rate setting means and said digital flow monitoring means for digitally regulating the pulse width of the output pulses to said electrical motor means.

73. A system as set forth in claim 72, wherein said digital memory means includes a pair of digital counters.

74. A system as set forth in claim 72, wherein said digital memory means includes a digital counter which undergoes successive counting cycles, a single counting cycle for each of said output pulses, the count state of said counter at the beginning of each of said counting cycles determining the pulse width of the corresponding output pulse produced during that counting cycle.

75. A system as set forth in claim 74, and further including:
means for decrementing said counter by a first prescribed number of counts during each counting cycle and for incrementing said counter by a second prescribed number of counts only during a counting cycle after a drop has been detected.

76. A system as set forth in claim 75, and further including:
means for increasing the number of counts by which said counter is decremented during each counting cycle to a larger number for each counting cycle during an initial start-up period of operation of said system.

77. A system as set forth in claim 72, wherein said digital memory means further comprises:
a first counter; and
a second counter having a counting cycle under the control of said first counter.

78. A system as set forth in claim 77, wherein said first and said second counters undergo successive counting cycles, one for each of said output pulses produced, the count state of said second counter at the beginning of each counting cycle determining the pulse width of the output pulse generated during that counting cycle.

79. A system as set forth in claim 78, wherein said second counter is decremented relative to said first counter by a first prescribed number of counts during each counting cycle, and said second counter is incremented relative to said first counter by a second prescribed number of counts only during a counting cycle after a drop has been detected.

80. In the parenteral administration of medical fluids by an intravenous set including drop forming means in a flexible tube coupled to said drop forming means for carrying drop flow, a method of controlling the rate of drop flow through the flexible tube, comprising the steps of:
clamping said tube to a substantially shut-off state;
producing digital control pulses in a pulse train at a selected frequency proportional to the desired rate of drop flow;
monitoring the actual drip flow occurring through said tube;
selectively varying the pulse width of each of said control pulses in a digital memory in accordance with the desired drop flow rate and the actual drop flow rate detected; and
repetitively opening and closing said tube to fluid flow in response to said digital control pulses to regulate the actual drop flow rate so that it conforms to said desired drop flow rate, said tube being closed during the periods between said control pulses in said pulse train.

81. A method as set forth in claim 80, wherein the frequency of opening said tube is a relatively high multiple of the desired drop flow rate.

82. A method as set forth in claim 81, wherein said multiple is approximately 10½ times the desired drop flow rate.

83. In a system for parenteral administration of medical liquids by drop flow through a feeding tube, apparatus comprising:
clamping means for clamping said feeding tube in a normally shut-off state;
electrical pulsing means for generating control pulses in a pulse train at a rate greater than the desired drop flow rate to periodically energize said clamping means and thereby open said tube to liquid flow, said clamping means being inactive during the periods between control pulses in said pulse train;
digital rate setting means for digitally establishing the frequency of said electrical pulsing means;
flow monitoring means for monitoring actual drop flow through said feeding tube and generating a digital electrical pulse each time a drop is detected; and
digital memory and timing means responsive to both said digital rate setting means and said flow monitoring means for digitally predetermining and varying the pulse width of the pulses from said pulsing means.

84. A system as set forth in claim 83, wherein said digital memory and timing means includes counting means.

85. A system as set forth in claim 83, wherein said digital memory and timing means includes a digital counter which undergoes successive counting cycles, one counting cycle for each of said output pulses, the count state of said counter at the beginning of each counting cycle determining the pulse width of the output pulse produced during that counting cycle.

86. A system as set forth in claim 85, wherein said counter is decremented by a first prescribed number of counts during each counting cycle and said counter is incremented by a second prescribed number of counts only during a counting cycle after a drop has been detected.

87. A system as set forth in claim 86, wherein the ratio of said second prescribed number of counts to said first prescribed number of counts is predetermined.

88. A system as set forth in claim 87, wherein said ratio is the same as the ratio of the frequency of said control pulses to the desired drop flow rate frequency.

89. A system as set forth in claim 88, wherein said ratio is $10\frac{1}{2}$.

90. A system as set forth in claim 88, and further including:
means for increasing the number of counts by which said counter is decremented during each counting cycle to a larger number for each counting cycle during an initial start-up period of operation of the system.

91. A system as set forth in claim 83, wherein said digital memory and timing means further comprises:
a first counter; and
a second counter having a counting cycle under the control of said first counter.

92. A system as set forth in claim 91, wherein said first and said second counters undergo successive counting cycles, one for each of said output pulses produced, the count state of said second counter at the beginning of each counting cycle determining the pulse width of the output pulse generated during that counting cycle.

93. A system as set forth in claim 92, wherein said second counter is decremented relative to said first counter by a first prescribed number of counts during each counting cycle, and said second counter is incremented relative to said first counter by a second prescribed number of counts only during a counting cycle after a drop has been detected.

94. In a system for parenteral administration of liquids at desired flow rates through a feeding tube from a liquid source to a patient, the combination comprising:
electromechanical output control means for manipulating the feeding tube to vary the flow of liquid in the feeding tube;
electrical pulsing means for providing output pulses to operate said output control means;
digital memory means for automatically varying the pulse width of said output pulses operating said control means, to achieve the desired flow rate, said digital memory means including a digital counter which undergoes successive counting cycles, a single counting cycle for each of said output pulses produced by said pulsing means, the count state of said counter at the beginning of each counting cycle determining the pulse width of the corresponding output pulse produced during that counting cycle;
means for decrementing said counter by a first prescribed number of counts during each of said counting cycles, and for incrementing said counter by a second prescribed number of counts only during a counting cycle after a drop of liquid flow has been detected; and
means for increasing said first prescribed number of counts by which said counter is normally decremented during each counting cycle to a larger prescribed number for each counting cycle during an initial start-up period of operation of said system.

95. In a system for parenteral administration of liquids at desired flow rates through a feeding tube from a liquid source to a patient, the combination comprising:
electromechanical output control means for manipulating the feeding tube to vary the flow of liquid in the feeding tube;
electrical pulsing means for providing output pulses to operate said output control means;
digital memory means for automatically varying the pulse width of said output pulses operating said control means, to achieve the desired flow rate, said digital memory means including a digital counter which undergoes successive counting cycles, a single counting cycle for each of said output pulses produced by said pulsing means, the count state of said counter at the beginning of each counting cycle determining the pulse width of the corresponding output pulse produced during that counting cycle;
means for monitoring the period between initiation of successive of said output pulses;
means for generating a duty cycle limitation signal at a predetermined time in each of said monitored periods; and
means for overriding said digital memory means when said duty cycle limitation signal is imposed.

96. A system as set forth in claim 95, and further comprising:
clocking means for generating two different clock rates, a normal clock rate and a higher clock rate.

97. A system as set forth in claim 96, wherein said duty cycle signal, if imposed during a counting cycle, switches the counting rate of said counter from said normal clock rate to said higher clock rate.

98. In a system for parenteral administration of liquids at desired flow rates through a feeding tube from a liquid source to a patient, the combination comprising:
electromechanical output control means for manipulating the feeding tube to vary the flow of liquid in the feeding tube;
electrical pulsing means for providing output pulses to operate said output control means;
digital memory means for automatically varying the pulse width of said output pulses operating said control means, to achieve the desired flow rate;
clocking means capable of generating clocking pulses at two different rates, a high rate and a low rate; and
means for automatically switching said clocking means from said low rate to said high rate at prescribed times in each period between initiation of successive of said output pulses.

99. In a system for parenteral administration of liquids at a desired drop flow rate through a feeding tube from a liquid source to a patient, the combination comprising:
output control means for determining the rate of drop flow of liquid in the feeding tube;
electrical pulsing means for providing successive output pulses to said output control means;
counting means for varying the pulse width of each of said output pulses, to achieve the desired drop flow rate;
means for monitoring the period between initiation of said successive output pulses;

means for generating a duty cycle limitation signal at a preselected time in each of said monitored periods; and means for overriding the pulse width determination by said counting means when said duty cycle limitation signal is imposed.

100. A system as set forth in claim 99, and further comprising:

clocking means for generating two different clock rates, a normal clock rate and a higher clock rate.

101. A system as set forth in claim 100, wherein said duty cycle signal, if imposed during a counting cycle, changes the counting rate of said counting means from said normal clock rate to said higher clock rate.

102. In a system for parenteral administration of liquids at a desired drop flow rate through a feeding tube from a liquid source to a patient, the combination comprising:

output control means for determining the rate of drop flow of liquid in the feeding tube;

electrical pulsing means for providing successive output pulses to said output control means;

counting means for varying the pulse width of each of said output pulses, to achieve the desired drop flow rate;

clocking means capable of generating clocking pulses at two different rates, a high rate and a low rate; and means for automatically switching said clocking means from said low rate to said high rate at prescribed times in each period between initiation of said successive output pulses.

* * * * *

UNITED STATES PATENT OFFICE
CERTIFICATE OF CORRECTION

Patent No. 4,037,598            Dated July 26, 1977

Inventor(s) HEINZ W. GEORGI

It is certified that error appears in the above-identified patent and that said Letters Patent are hereby corrected as shown below:

In the Abstract: line 4, delete "varible" and insert therefor --variable--.

Column 3, line 38, delete "(cycle)" and insert therefor --cycle)--.

Column 5, line 45, after "pulse" insert --width--; line 66, after "subsystem" insert --system--.

Column 7, line 26, delete "invention" and insert therefor --inventor--; line 64, delete "pump" and insert therefor --pumping--.

Column 8, line 11, after "be" insert --of the--; line 31, after "open" insert --loop--; after "digital" insert --command--; line 37, delete "19" and insert therefor --20--; line 42, delete "desire" and insert therefor --desired--; line 45, delete "10-In" and insert therefor --10-1/2. In--; line 53, after "using" insert --an--.

Column 9, line 7, after "output" (first occurrence), insert --pulse--; line 26, delete "register" (second occurrence) and insert therefor --registers--; line 48, before "next", insert --very--; after "output", insert --pulse--; line 64, delete "whe" and insert therefor --when--; line 65, begin a new paragraph with the word "In".

Column 10, line 9, before "number", delete "th" and insert therefor --the--; line 56, delete "th" and insert therefor --the--.

UNITED STATES PATENT OFFICE
CERTIFICATE OF CORRECTION

Page 2 of 4

Patent No. 4,037,598                    Dated July 26, 1977

Inventor(s) HEINZ W. GEORGI

It is certified that error appears in the above-identified patent and that said Letters Patent are hereby corrected as shown below:

Column 11, line 24, after "of" delete "th" and insert therefor --the--; line 64, delete "featue" and insert therefor --feature--.

Column 12, line 4, delete "sidreably" and insert therefor --siderably--; line 11, delete "produced" and insert therefor --produce--; line 46, delete "suitble" and insert therefor --suitable--; line 53, delete "th" and insert therefor --the--.

Column 13, line 9, delete "th" and insert therefor --the--.

Column 15, line 36, delete ""zone"" and insert therefor --"zero"--.

Column 16, line 59, delete "ca" and insert therefor --can--.

Column 17, line 21, delete "(21/2" and insert therefor --21/2--.

Column 18, line 13, delete "millisecond" and insert therefor --milliseconds--; line 56, delete "illustrte" and insert therefor --illustrate--.

Column 19, line 11, delete "parenthes" and insert therefor --parentheses--.

Column 20, line 15, delete "to".

UNITED STATES PATENT OFFICE
CERTIFICATE OF CORRECTION

Page 3 of 4

Patent No. 4,037,598                    Dated July 26, 1977

Inventor(s) HEINZ W. GEORGI

It is certified that error appears in the above-identified patent and that said Letters Patent are hereby corrected as shown below:

Column 21, line 7, delete " "" " and insert --"1"--.
line 26, delete "pulse" and insert --pulses --.

Column 23, line 42, after "width" insert --register--.

Column 25, line 44, delete "primarly" and insert therefor --primary--.

Column 26, line 4, after "liquid" insert --typically--; line 36, delete "is" (first occurrence).

Column 27, line 1, delete "steppping" and insert therefor --stepping--; line 22, delete "decribed" and insert therefor --described--.

Column 30, line 46, after "wide" insert --pulse--; line 55, delete "proceding" and insert therefor --preceding--; line 57, delete "Asseming" and insert therefor --Assuming--.

Column 31, line 45, after "DRZ" insert --pulse--; line 66, delete "miximum" and insert therefor --maximum--.

Column 32, line 12, after "except" insert --that--.

Column 33, line 1, delete "get" and insert therefor --gets--; line 19, delete "incicates" and insert therefor --indicates--.

UNITED STATES PATENT OFFICE
CERTIFICATE OF CORRECTION

Page 4 of 4

Patent No. 4,037,598  Dated July 26, 1977

Inventor(s) HEINZ W. GEORGI

It is certified that error appears in the above-identified patent and that said Letters Patent are hereby corrected as shown below:

Column 34, line 23, after "other" insert --output--; line 32, delete "Q" and insert therefor --$\overline{Q}$--; line 43, delete "decorder" and insert therefor --decoder--.

Column 35, line 7, before "gate" insert --pulse--; line 24, delete "countered" and insert therefor --counted--.

Column 36, line 66, before "flow" insert --and--.

Column 37, line 16, delete "active" and insert therefor --inactive--.

Column 44, line 24, delete "drip" and insert therefor --drop--.

Signed and Sealed this

Third Day of January 1978

[SEAL]

Attest:

RUTH C. MASON  
Attesting Officer

LUTRELLE F. PARKER  
Acting Commissioner of Patents and Trademarks